United States Patent
Kim et al.

(10) Patent No.: US 10,105,463 B2
(45) Date of Patent: Oct. 23, 2018

(54) ULTRAVIOLET (UV) STERILIZATION MODULE AND AIR CONDITIONER INCLUDING UV STERILIZATION MODULE

(71) Applicant: LG ELECTRONICS INC., Seoul (KR)

(72) Inventors: Taeyoung Kim, Seoul (KR); Gyoungsoo Kim, Seoul (KR)

(73) Assignee: LG ELECTRONICS, INC., Seoul (KR)

( * ) Notice: Subject to any disclaimer, the term of this patent is extended or adjusted under 35 U.S.C. 154(b) by 80 days.

(21) Appl. No.: 15/299,622

(22) Filed: Oct. 21, 2016

(65) Prior Publication Data
US 2018/0021468 A1 Jan. 25, 2018

(30) Foreign Application Priority Data
Jul. 22, 2016 (KR) .......................... 10-2016-0093754

(51) Int. Cl.
| | |
|---|---|
| A61L 9/20 | (2006.01) |
| F24F 1/00 | (2011.01) |
| F24F 13/30 | (2006.01) |
| F24F 13/28 | (2006.01) |
| F24F 13/20 | (2006.01) |

(52) U.S. Cl.
CPC .............. *A61L 9/20* (2013.01); *F24F 1/0007* (2013.01); *F24F 1/0025* (2013.01); *F24F 13/20* (2013.01); *F24F 13/28* (2013.01); *F24F 13/30* (2013.01); *A61L 2209/15* (2013.01); *F24F 2001/004* (2013.01); *F24F 2001/0037* (2013.01); *F24F 2001/0048* (2013.01)

(58) Field of Classification Search
USPC ................... 250/436, 455.11, 454.11, 432 R; 422/122, 120, 186.3
See application file for complete search history.

(56) References Cited

U.S. PATENT DOCUMENTS

| | | |
|---|---|---|
| 5,043,634 A | 8/1991 | Rothwell, Jr. et al. |
| 5,558,158 A | 9/1996 | Elmore |
| 5,993,749 A | 11/1999 | Adams |

(Continued)

FOREIGN PATENT DOCUMENTS

| | | |
|---|---|---|
| KR | 10-2003-0091688 | 12/2003 |
| KR | 10-2005-0083416 | 8/2005 |

(Continued)

OTHER PUBLICATIONS

United States Office Action dated Sep. 7, 2017 issued in U.S. Appl. No. 15/368,920.

(Continued)

*Primary Examiner* — Kiet T Nguyen
(74) *Attorney, Agent, or Firm* — Ked & Associates, LLP

(57) ABSTRACT

An ultraviolet (UV) sterilization module and an air conditioner including a UV sterilization module are provided. The UV sterilization module may include a porous main body; a plurality of UV lamps having external electrodes; a plurality of conductive holders connected to the external electrodes and that supports the plurality of UV lamps to be spaced from the porous main body; and at least one bus bar connected to the plurality of conductive holders and provided between the plurality of conductive holders and the porous main body.

24 Claims, 22 Drawing Sheets

(56) References Cited

U.S. PATENT DOCUMENTS

| | | |
|---|---|---|
| 6,685,890 B1 | 2/2004 | Van Remmen |
| 7,773,081 B2 | 8/2010 | Olson |
| 7,852,005 B2 | 12/2010 | Misono et al. |
| 8,018,130 B2 | 9/2011 | Van Den Broek et al. |
| 8,124,012 B2 | 2/2012 | Leroux et al. |
| 8,232,715 B2 | 7/2012 | Kusunoki et al. |
| 8,269,420 B2 | 9/2012 | Morizawa et al. |
| 8,304,974 B2 | 11/2012 | Watanabe et al. |
| 8,475,725 B1 | 7/2013 | Antipenko et al. |
| 2003/0217561 A1 | 11/2003 | Shindo et al. |
| 2003/0230477 A1 | 12/2003 | Fink et al. |
| 2004/0140269 A1 | 7/2004 | Chang |
| 2004/0232846 A1 | 11/2004 | Fischer et al. |
| 2004/0251810 A1 | 12/2004 | Hsu |
| 2005/0186124 A1 | 8/2005 | Fink et al. |
| 2006/0096459 A1 | 5/2006 | Iwano et al. |
| 2006/0113885 A1 | 6/2006 | Iimura |
| 2006/0263275 A1 | 11/2006 | Lobach |
| 2008/0030654 A1 | 2/2008 | Slutsky et al. |
| 2008/0073565 A1 | 3/2008 | Jeon |
| 2008/0092742 A1* | 4/2008 | Marra ............... B60H 1/008 96/16 |
| 2008/0274018 A1* | 11/2008 | Kawai ............... A01M 29/12 422/122 |
| 2008/0286163 A1* | 11/2008 | Garfield ............ A61L 9/205 422/120 |
| 2009/0168433 A1 | 7/2009 | Frick |
| 2010/0134000 A1 | 6/2010 | Carter et al. |
| 2011/0227501 A1 | 9/2011 | Awamoto et al. |
| 2012/0085927 A1 | 4/2012 | Maeng et al. |
| 2012/0153804 A1 | 6/2012 | Li |
| 2012/0199005 A1 | 8/2012 | Koji et al. |
| 2012/0319011 A1 | 12/2012 | Brabham et al. |
| 2013/0192288 A1 | 8/2013 | Willette |
| 2014/0157989 A1 | 6/2014 | Kirschman |
| 2015/0228470 A1 | 8/2015 | Ruiz |
| 2015/0262780 A1 | 9/2015 | Eaton |

FOREIGN PATENT DOCUMENTS

| | | |
|---|---|---|
| KR | 10-2006-0035144 | 4/2006 |
| KR | 10-2006-0039360 | 5/2006 |
| KR | 10-0725763 | 5/2007 |

OTHER PUBLICATIONS

U.S. Appl. No. 15/368,920, filed Dec. 5, 2016.
U.S. Appl. No. 15/363,036, filed Nov. 29, 2016.
U.S. Appl. No. 15/363,071, filed Nov. 30, 2016.
U.S. Appl. No. 15/371,418, filed Dec. 7, 2016.
U.S. Office Action dated Aug. 3, 2017 issued in U.S. Appl. No. 15/363,071.
U.S. Office Action issued in U.S. Appl. No. 15/363,036 dated Jun. 27, 2018.

* cited by examiner (mW/cm²)

ULTRAVIOLET (UV) STERILIZATION MODULE AND AIR CONDITIONER INCLUDING UV STERILIZATION MODULE

CROSS-REFERENCE TO RELATED APPLICATION(S)

The present application claims priority under 35 U.S.C. 119 and 35 U.S.C. 365 to Korean Patent Application No. 10-2016-0093754, filed in Korea on Jul. 22, 2016, which is hereby incorporated by reference in its entirety.

BACKGROUND

1. Field

An ultraviolet (UV) sterilization module and an air conditioner including a UV sterilization module.

2. Background

Generally, an air conditioner controls at least one of a temperature, a humidity, or a purification of an indoor air to generate a conditioned air to be suitable for a user. The air conditioner may use a refrigerating cycle of a refrigerant to control a temperature, and a humidity. The air conditioner may include a compressor, a condenser, an expander, and an evaporator as a refrigerant flow path. Indoor air may be suctioned via an inlet to the condenser or the evaporator in which the air is subject to heat exchange and then the air may be discharged via an air outlet.

The air conditioner may include a filter or dust collector to control a purification level of the air. Further, indoor air may be suctioned via an air inlet into the air conditioner and then may be purified using a purification unit or device. The purified air may be discharged via an air outlet out of the air conditioner.

Recently, a UV sterilizer device has been provided in the air conditioner to purify the air in the air conditioner. One example of this approach is disclosed in KR application publication No. 10-2006-0035144 published on Apr. 26, 2006, which is hereby incorporated by reference and in which a UV sterilizer device extends along one surface of the heat exchanger. This prior art UV sterilizer device has a large UV lamp, and thus, has a shortcoming in terms of a space efficiency and air channel. When the larger UV lamp is disposed on the surface of the heat exchanger, the air may not be sterilized uniformly along the front of the heat exchanger.

BRIEF DESCRIPTION OF THE DRAWINGS

Embodiments will be described in detail with reference to the following drawings in which like reference numerals refer to like elements, and wherein.

DETAILED DESCRIPTION

Figure 1:
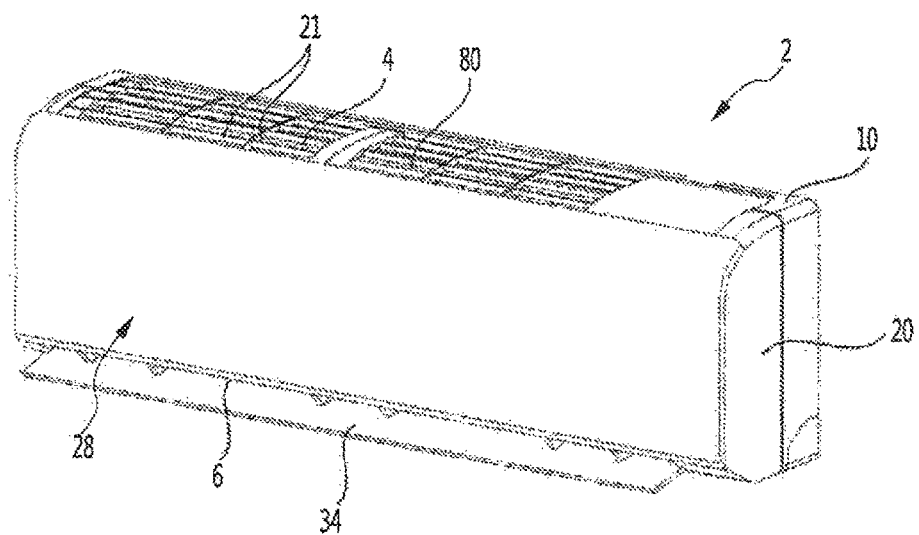
FIG. 1 is a perspective view of an air conditioner according to an embodiment in a turned-on state.

Examples of various embodiments are illustrated in the accompanying drawings and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

Example embodiments will be described in more detail with reference to the accompanying drawings. The present disclosure, however, may be embodied in various different forms, and should not be construed as being limited to only the illustrated embodiments herein. Rather, these embodiments are provided as examples so that this disclosure will be thorough and complete, and will fully convey the aspects and features of the present disclosure to those skilled in the art.

It will be understood that when an element or layer is referred to as being "connected to", or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, s, operations, elements, and/or components, but do not preclude the presence or addition of one or more other features, integers, s, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Spatially relative terms, such as "beneath," "below," "lower," "under," "above," "upper," and the like, may be used herein for ease of explanation to describe one element or feature's relationship to another element s or feature s as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented for example, rotated 90 degrees or at other orientations, and the spatially relative descriptors used herein should be interpreted accordingly.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the following description, numerous specific details are set forth in order to provide a thorough understanding of the present disclosure. The present disclosure may be practiced without some or all of these specific details. In other instances, well-known process structures and/or processes have not been described in detail in order not to unnecessarily obscure the present disclosure.

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

Hereinafter, embodiments will be described with reference to attached drawings.

Figure 2:
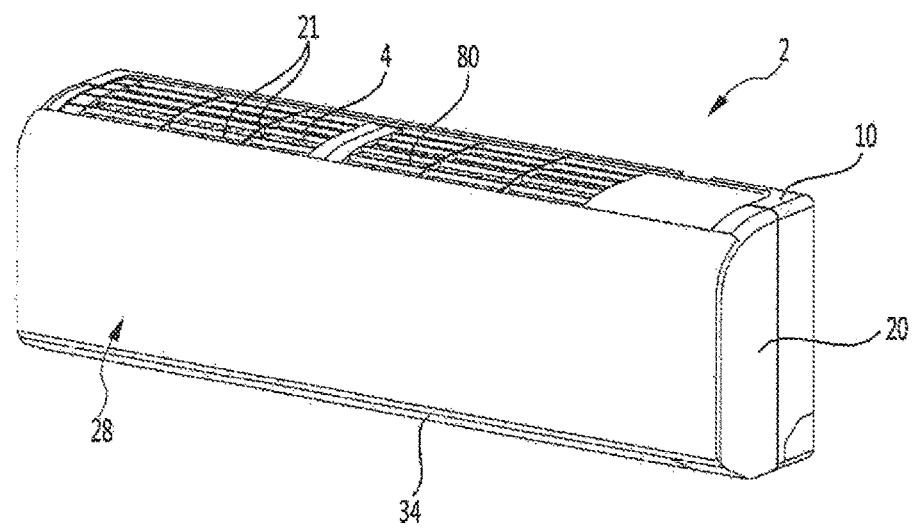
FIG. 2 is a perspective view of the air conditioner according to an embodiment in a turned-off state.
Figure 3:
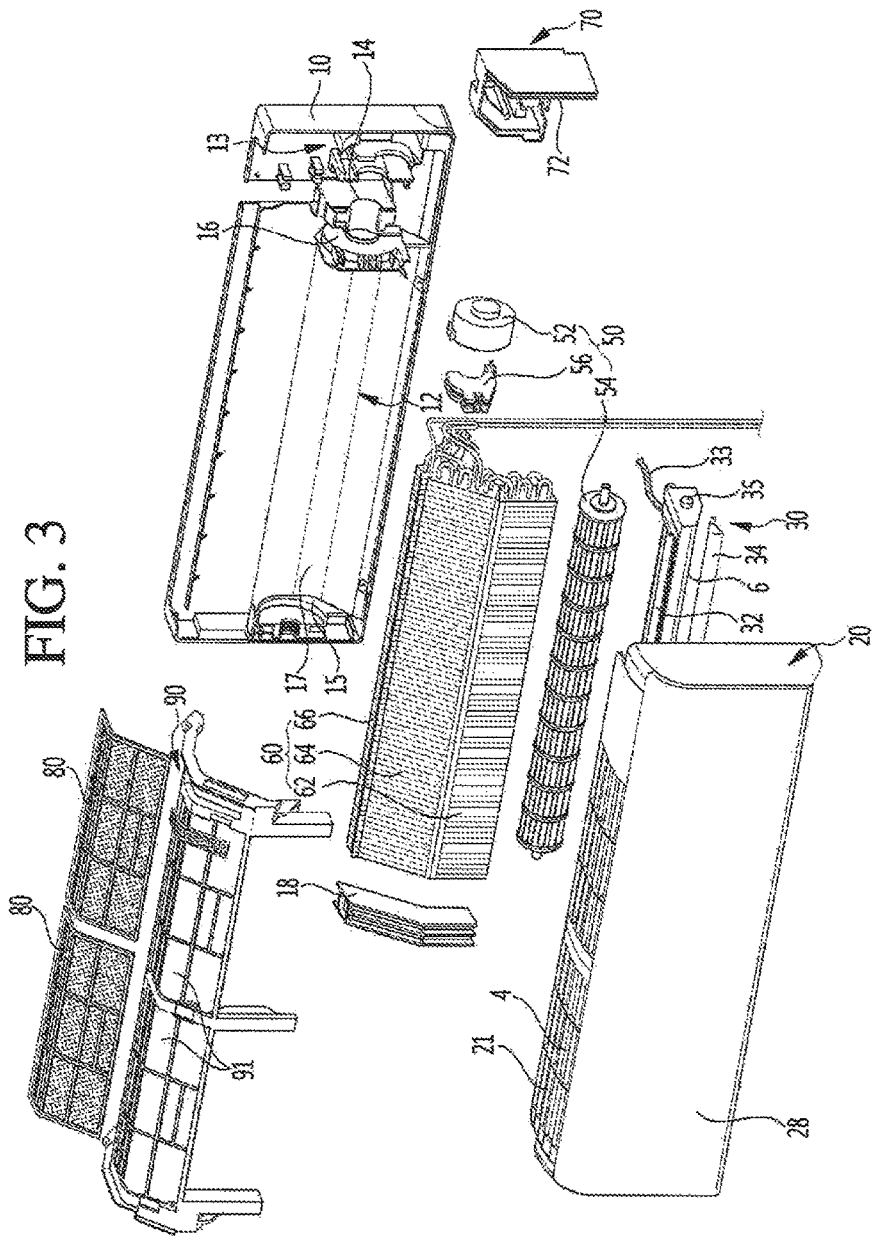
FIG. 3 is an exploded perspective view of the air conditioner according to an embodiment.
Figure 4:
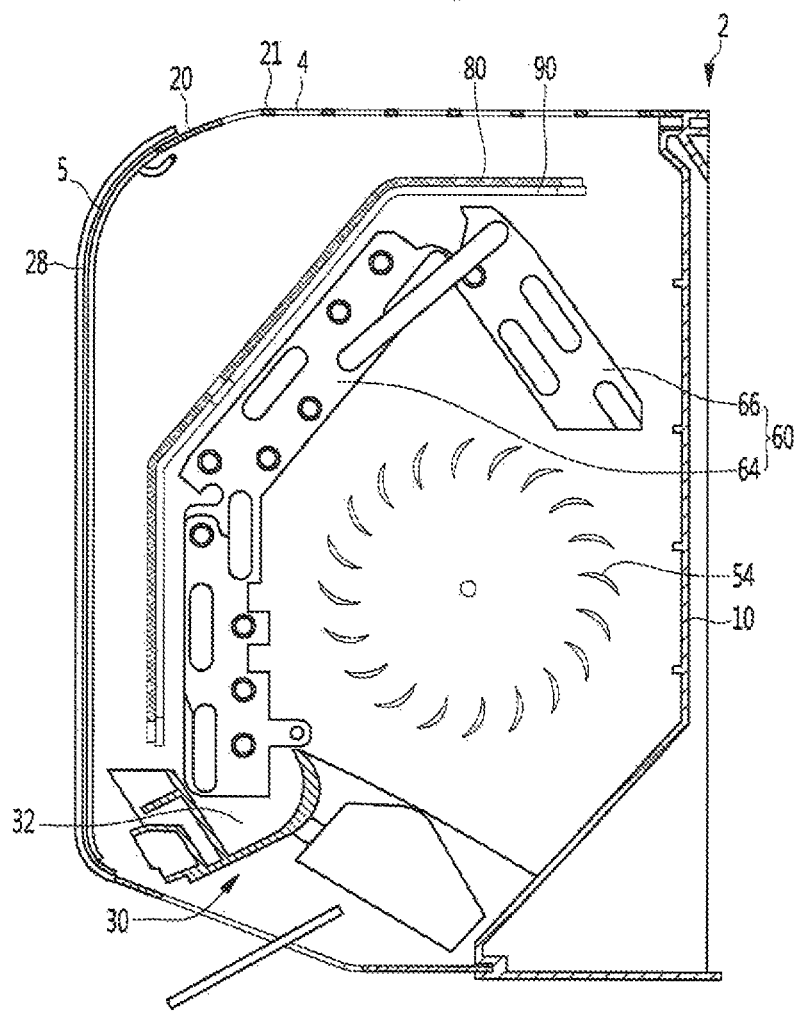
FIG. 4 is a vertical cross-sectional view illustrating a state when a wind-direction adjustment member in FIG. 1 discharges and guides conditioned air to an indoor upper space.

FIG. 1 is a perspective view of an air conditioner according to an embodiment in a turned-on state. FIG. 2 is a perspective view of an air conditioner of FIG. 1 in a turned-off state. FIG. 3 is an exploded perspective view of the air conditioner of FIG. 1. FIG. 4 is a vertical cross-sectional view illustrating a state when a wind-direction adjustment member or adjuster in FIG. 1 discharges and guides a conditioned air to an indoor upper space.

In this embodiment, the air conditioner may include a main body 2 having an air inlet 4 to receive indoor air and an air outlet 6 to discharge conditioned air. In this embodiment, the air conditioner may be configured to receive air from the air inlet 4 and to condition the air therein and then to discharge the conditioned air via the air outlet 6. The air conditioner may be implemented as a stand-type air conditioner, a ceiling-mounted air conditioner, or a wall-mounted air conditioner, for example. Hereinafter, a reference may be made to a wall-mounted air conditioner by way of example.

The main body 2 may be installed or provided indoors and may be a singular component or a combination of multiple components. In the latter case, the main body 2 may include a chassis 10, a front frame 20, a suction grill 21, a front panel 28, and a discharge unit or device 30. Hereinafter, the chassis 10 may be referred to as a rear frame 10.

In the main body 2, the air inlet 4 may be formed in or at front and top portions thereof and the air outlet 6 may be formed in or at a bottom portion thereof. The front panel 28 may move in a front-rear direction or may pivot downward or upward to form an air suction channel between the front surface and the front panel 28.

Alternatively, in the main body 2, the air inlet 4 may be formed in or at a top portion thereof and the air outlet 6 may be formed in or at a bottom portion thereof. The main body 2 may have an opening for maintenance of the conditioner at the front portion thereof, and the front panel 28 may be arranged to open and close the front surface and the opening of the main body 2.

Hereinafter, a reference will be made to an example in which the air inlet 4 is formed at a top portion of the main body 2, and the air outlet 6 is formed at a bottom portion of the main body 2. The front panel 28 may be formed as a front appearance of the air conditioner and may be configured to pivot around an upper edge thereof or to move in a front-rear direction.

The chassis 10 may be mounted to a wall and may define an air flow channel therein. The chassis 10 may be function as a housing or rear frame to receive various components.

The chassis 10 may have a wind channel guide 12 formed therein to guide an air from the air inlet 4 to the air outlet 6. At one of first and second or left and right sides of the wind channel guide 12, an electronics board 13 may be disposed or provided on which various electronic components may be mounted.

The wind channel guide 12 may define an air channel for a fan 54, which is discussed hereinafter. The wind channel guide 12 may include first and second or left and right guides 15, 16 expanding in a front direction from the chassis 10, and a middle guide 17 between the left and right guides 15, 16. At one of the left and right guide 15, 16, a heat exchanger supporter 18 may be disposed or provided to support a heat exchanger 60 and to define an air channel. From the electronics board 13, a motor installation 14 may protrude in a frontward direction to receive a fan motor 52. On the electronics board 13, a control box 70 may be disposed or provided to control the air conditioner. The control box 70 may be disposed or provided together with a controller (not shown) for the fan motor 52 of an air blower 50, and a wind-direction adjustment member driver 35, for example.

The front frame 20 may be provided at a front of the chassis 10 to define a space with the chassis 10. The front frame 20 may define a wind channel with the wind channel guide 12 of the chassis 10, and may cover the electronics board 13 on the chassis 10 to protect the electronics board 13. The front frame 20 may have openings in top and front portions thereof. The opening in the top portion may act as the air inlet 4. A front opening 5 may act as an access passage for a filter 80 or UV sterilization module or sterilizer 760.

The front frame 20 may have the front opening 5 in a front of the wind channel guide 12 of the chassis 10. An upper opening may be formed at an upper portion in a front of the wind channel guide 12 of the chassis 10.

The suction grill 21 may allow indoor air to be suctioned into the main body 2 and may protect a bottom of the body. The suction grill 21 may be formed in a grill shape on the top opening of the front frame 20.

The discharge unit 30 may discharge conditioned air out of the main body 2. The discharge unit 30 may be assembled to at least one of the chassis 10 or the front frame 20 via a fastener or a hook.

On or at a top of the discharge unit 30, a drain 32 may be provided to collect condensed water falling from the heat exchanger 60. The drain 32 may be coupled to a drain connection hose 33 to guide the condensed water out of the main body 2. The air outlet 6 may be formed on the bottom of the drain 32.

The discharge unit 30 may have a wind-direction adjuster to control a wind-direction of air passing through the air outlet 6. The wind-direction adjuster may guide the air passing through the air outlet 6 and control the wind-direction. The wind-direction adjuster may include a wind-direction adjustment member or adjuster 34 rotatably disposed or provided at the main body 2, more particularly, at the discharge unit 30, and the wind-direction adjustment member driver 35 to rotate the wind-direction adjustment member 34.

The wind-direction adjustment member 34 may include a horizontal wind-direction adjustment member or adjuster to control a horizontal wind-direction of the air passing through the air outlet 6, and a vertical wind-direction adjustment member or adjuster to control a vertical wind-direction of the air passing through the air outlet 6. The wind-direction adjustment member driver 35 may be coupled to the horizontal wind-direction adjustment member to allow the horizontal wind-direction adjustment member to rotate around a vertical axis. Further, the wind-direction adjustment member driver 35 may be coupled to the vertical wind-direction adjustment member to allow the vertical wind-direction adjustment member to rotate around a horizontal axis.

The wind-direction adjustment member 34 may rotate to allow one of the horizontal wind-direction adjustment member or vertical wind-direction adjustment member to open and close the air outlet 6. Hereinafter, a reference will be made to a configuration where the vertical wind-direction adjustment member closes and opens the air outlet 6, the wind-direction adjustment member driver 35 is provided at one of first and second or left and right sides of the discharge unit 30 to drive the rotation of the vertical wind-direction adjustment member as a wind-direction adjustment motor.

The main body 2 may receive the air blower 50 to suction the air into the air inlet 4 and move the air into the main body 2 and discharge the air to the air outlet 6. Further, the main body 2 may receive the heat exchanger 60 to allow heat exchange between the air and refrigerant. Further, the main body 2 may receive the filter 80 to purify the air suctioned into the air inlet 4 and a filter frame 90 for the filter 80.

The air blower 50 may include the fan motor 52 seated in the motor installation 14 formed in the chassis 10, more particularly, the electronics board 13, and the fan 54 disposed or provided at a rotation axis of the fan motor 52 and located on the wind channel guide 12. The fan 54 may be implemented as a horizontally-elongated cross flow fan between the wind channel guides 15,16,17, more particularly, between the left and right channel guides 15,16. The air blower 50 may further include a motor cover 56 disposed or provided at the chassis 10 to cover the fan motor 52.

The heat exchanger 60 may be located between the air inlet 4 and the fan 54. For this, the heat exchanger 60 may be located at a rear of the front frame 20 and may have a lower end disposed or provided on or at a top of the drain 32. The heat exchanger 60 may include a vertical portion 62 on or at the top of the drain 32, a front tilted portion 64 from a top of the vertical portion 62 to a top of a rear portion, and a rear tilted portion 66 from a top of the front tilted portion 64 to a bottom of a rear portion.

The filter frame 90 may be provided between the air inlet 4 and the heat exchanger 60. The filter frame 90 may have openings 91 formed therein to receive the filter 80.

In this embodiment, the air conditioner may include a controller (not shown) provided in the main body 2 to control the fan motor 52, and the wind-direction adjustment member driver 35, for example. The controller may control the fan motor 52 and wind-direction adjustment member driver 35 during an air cooling operation. A cool conditioned air may be guided to the wind-direction adjustment member 34 and then be discharged therefrom. The wind-direction adjustment member 34 may spread the conditioned air via a rotation thereof. In an opening mode of the wind-direction adjustment member driver 35, the wind-direction adjustment member 34 may open the air outlet 6 via a rotation of the wind-direction adjustment member driver 35. The rotation of the fan motor 52 may rotate the fan 54. The rotation of the fan 54 may allow the indoor air to be suctioned via the air inlet 4 into the main body 2 and then to be purified via the filter 80 and then to heat exchange with the heat exchanger 60. Then, the air may pass through the air outlet 6 via the wind-direction adjustment member 34 and then be discharged therefrom.

In a swing discharge mode, the controller may allow forward/reverse rotations of the wind-direction adjustment member driver 35 during the rotation of the fan motor 52. Further, the wind-direction adjustment member 34 may translate vertically via the wind-direction adjustment member driver 35 to allow a vertical spreading of the air passing through the air outlet 6.

Figure 5:
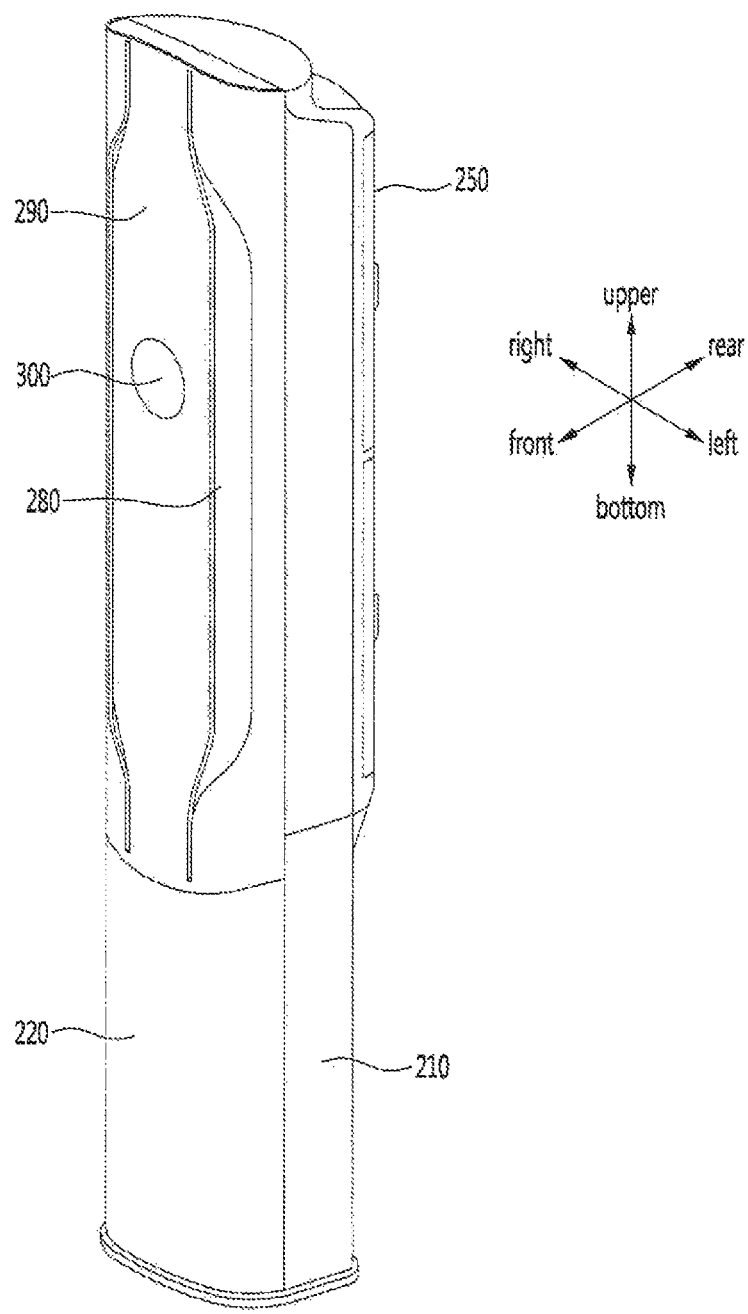
FIG. 5 is a perspective view of an air conditioner according to another embodiment.
Figure 6:
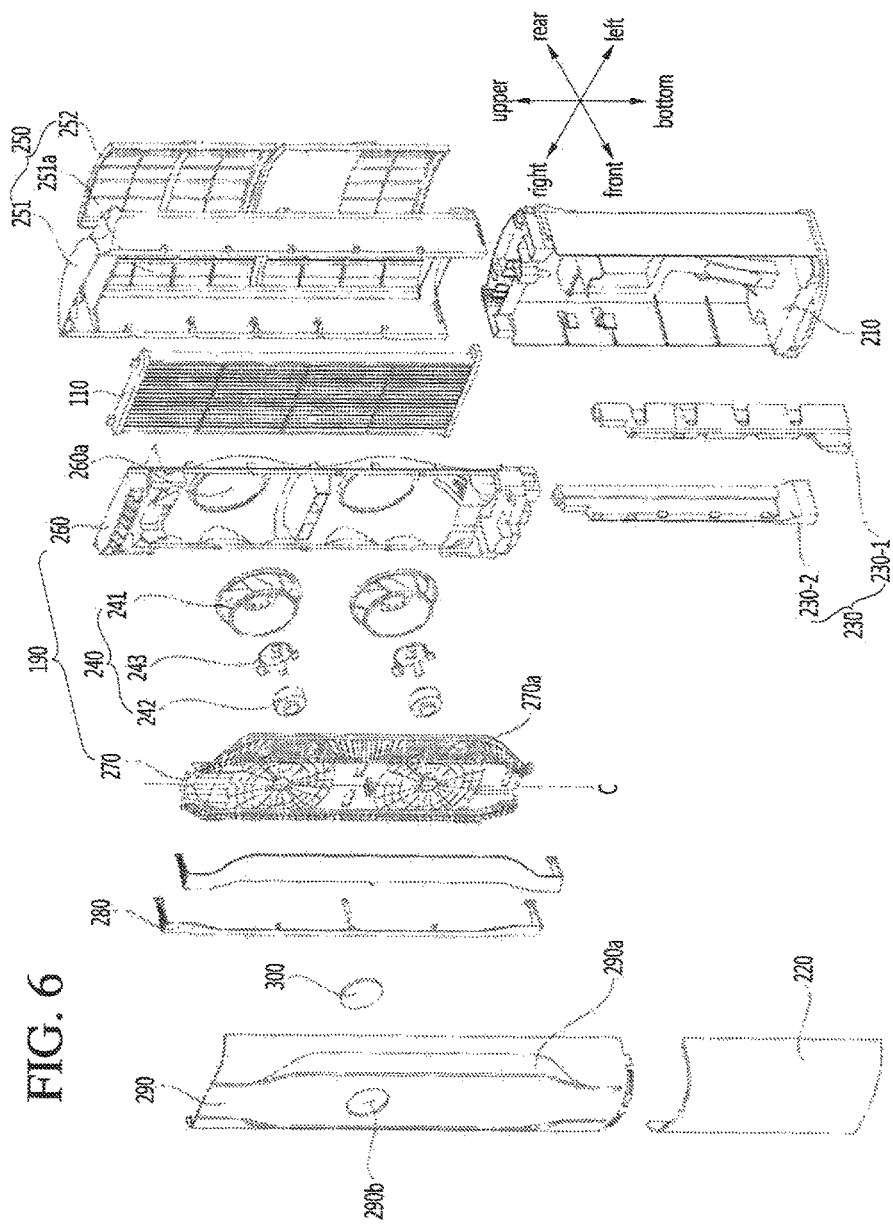
FIG. 6 is an exploded perspective view of the air conditioner of FIG. 5.

FIG. 5 is a perspective view of an air conditioner according to another embodiment. FIG. 6 is an exploded perspective view of the air conditioner of FIG. 5.

In this embodiment, the air conditioner is implemented as a stand-type air conditioner. The stand-type air conditioner may include a base rear panel 210 that contacts a floor and having an inner space therein, and a main body rear panel 250 coupled to a top of the base rear panel 210 and having an air inlet 251*a* formed therein. Further, the stand-type air conditioner may include one or more connector 230 coupled to the base rear panel 210 at an inside thereof, and a base front panel 220 coupled to the connector 230. Further, the stand-type air conditioner may include a main body front panel 290 coupled to the base front panel 220 at a bottom thereof and coupled to the main body rear panel 250 at a side portion thereof and having an air outlet 290*a*.

The base rear panel 210 may be supported on a floor on which the air conditioner is installed or provided. The base rear panel 210 may have an inner space defined therein. For this, the base rear panel 210 may have a polyhedral shape with an open front portion. The base rear panel 210 may have a curved rear surface. The base rear panel 210 may have a bottom that contacts the floor.

The base rear panel 210 may have an inner side wall coupled to the connector 230. In the inner space in the base rear panel 210, a circuit element to control the air conditioner, and an electronics box (not shown) to receive various electronic components may be provided. The base rear panel 210 may have a front portion coupled to the base front panel 220. The base rear panel 210 may have a top portion coupled to the main body rear panel 250.

The connector 230 may be coupled to the base rear panel 210 at an inner side thereof. The connector 230 may have a vertical elongate column shape. A plurality of the connector 230 may be provided. The plurality of the connector 230 may include a first or left connector 230-1 coupled to an inner first or left surface of the base rear panel 210, and a second or right connector 230-2 coupled to an inner second or right surface of the base rear panel 210. The left connector 230-1 and right connector 230-2 may be horizontally symmetrical.

The connector 230 may reinforce a strength of the base rear panel 210, and may support a shroud panel 260 having one or more air blowing module 240 and a guide panel 270 coupled thereto. The connector 230 may be coupled to the base rear panel 210 at a bottom and a partial side surface of the connector 230. The connector 230 may be coupled to the shroud panel 260 at a top of the connector 230. The connector 230 may be coupled to the base front panel 220 at a front of the connector 230.

The main body rear panel 250 may be coupled to a top of the base rear panel 210 to form an upper rear appearance of the air conditioner. The main body rear panel 250 may be formed of a hollow polyhedral shape with open front and rear surfaces.

The main body rear panel 250 may have the air inlet 251*a* to suction indoor air therein. The inlet 251*a* may be formed in a rear portion of the main body rear panel 250. The air blowing module 240 may be turned on to generate an air flow. Thus, the air may be suctioned into the inlet 251*a* and then the air may pass through an indoor heat exchanger 110 to the shroud panel 260.

The main body rear panel 250 may include a main body rear panel body 251 having the inlet 251*a* formed at a rear portion thereof, and a rear panel filter 252 mounted to the main body rear panel body 251 at a rear portion thereof to cover the inlet 251*a*. The rear panel filter 252 may filter the suctioned air into the inlet 251*a*. The rear panel filter 252 may be coupled to the main body rear panel body 251 at a rear thereof. The main body rear panel 250 may be coupled to the shroud panel 260 at a front of the panel 250. The main body rear panel 250 may be coupled to the base rear panel 210 at a bottom of the panel 250.

In the main body rear panel 250, the indoor heat exchanger 110 may be disposed or provided. The indoor heat exchanger 110 may be provided between the main body rear panel 250 and the shroud panel 260 to allow heat exchange between the air flowing into the inlet 251*a* of the main body rear panel 250 and a refrigerant. The air may be cooled or heated via the heat exchange with the refrigerant in the indoor heat exchanger 110 and then may be passed to the shroud panel 260. The indoor heat exchanger 110 may be implemented as a combination of a tube and fins. In the tube, the refrigerant may flow. The fins may realize the heat exchange.

The air blowing module 240 may suction air into the inlet 251*a* of the main body rear panel 250 and discharge the air via the air outlet 290*a* in the main body front panel 290. When the air blowing module 240 turns on, the air suctioned into the inlet 251*a* may pass through the indoor heat exchanger 110 and move through a shroud hole 260*a* in the shroud panel 260 to the air blowing module 240. Then, the air blowing module 240 may blow the air to move through a guide hole 270*a* of a guide panel 270 to the outlet 290*a* of the main body front panel 290.

A plurality of the air blowing module 240 may be provided. In this embodiment, a number of the air blowing module 240 is 2; however, embodiments are not limited thereto. In this embodiment, the two air blowing modules 240 are arranged vertically. The two air blowing modules 240 may correspond to two shroud holes 260*a* in the shroud panel 260, respectively. The two air blowing modules 240 may be coupled to the guide panel 270 at a rear of the panel 270.

The air blowing module 240 may include an air blower motor 242, an air blower motor bracket 243 to couple the air blower motor 242 to the guide panel 270 at a rear of the panel 270, and an air blowing fan 241 to rotate together with a rotation of the air blower motor 242 to create a flow of air. The air blowing fan 241 may be implemented as a centrifugal fan to receive air axially and then discharge the air radially. The air blowing fan 241 may be configured such that an air suction direction may be oriented toward the shroud hole 260*a* of the shroud panel 260. After the air is radially discharged from the air blowing fan 241, the air may flow toward a front of the shroud panel 260 and then pass through the guide hole 270*a* of the guide panel 270. When a plurality of air blowing modules 240 is provided, a plurality of the air blowing fan 241 may be provided. Further, the plurality of the air blowing fans 241 may correspond to the plurality of shroud holes 260*a*, respectively.

The shroud panel 260 may be configured to guide the air from the inlet 251a in main body rear panel 250 to the air blowing module 240. The shroud panel 260 may define the shroud hole 260a therein, through which the air from the indoor heat exchanger 110 may move to the air blowing module 240. A plurality of the shroud hole 260a may be provided. The plurality of the shroud holes 260a may correspond to the plurality of air blowing modules 240, respectively. In this embodiment, two shroud holes 260a may be vertically arranged to correspond to the two air blowing modules 240 respectively.

A surrounding portion of the shroud hole 260a of the shroud panel 260 may be formed in a dome shape to receive the air blowing module 240 therein. Thus, using the air blowing module 240, the flowing air may be guided to the front thereof.

The shroud panel 260 may be coupled to the connector 230 at a bottom of the panel 260. The shroud panel 260 may be coupled, at a rear thereof, to the main body rear panel 250. The shroud panel 260 may be coupled, at a front thereof, to the guide panel 270.

The guide panel 270 may be configured to guide flowing air using the air blowing module 240 to the outlet 290a. The guide panel 270 may have the air guide hole 270a defined therein to guide the air from the air blowing module 240 to the outlet 290a. A plurality of the guide hole 270a may be provided. In this embodiment, two guide holes 270a may be formed at lateral sides relative to a central line C, respectively. Each guide hole 270a may be vertically elongated. Each guide hole 270a may taper from a middle point to bottom and top points, respectively. Each guide hole 270a may be bent toward the central line C at upper and lower portions thereof. The guide hole 270a may be opened or closed by a door 280. Thus, when a plurality of the guide hole 270a is provided, a plurality of doors 280 may be provided.

The guide panel 270 may have the air blowing module 240 mounted thereto at a rear of the panel 270. In this embodiment, two air blowing modules 240 are vertically coupled to the rear portion of the guide panel 270. In a front of the guide panel 270, the door 280 may be provided. In this embodiment, in a front of the guide panel 270, two doors 280 are horizontally arranged.

The guide panel 270 may be at least partially curved such that the door 280 rotates and slides on and along the guide panel 270. In this embodiment, two doors 280 are horizontally arranged, and thus, the guide panel 270 may have a curved front portion at each of lateral sides relative to the vertical central line C. In other words, the curved front portion may be convex toward a front direction to form an arc shape.

The guide panel 270 may be coupled to the shroud panel 260 with the air blowing module 240 being interposed therebetween, thereby to form a single unit. In this embodiment, the guide panel 270, the air blowing module 240, and the shroud panel 260 may be collectively referred to as an air blowing unit or blower 190. That is, the air blowing unit 190 may include the guide panel 270, the air blowing module 240, and the shroud panel 260.

The door 280 may open or close the guide hole 270a and the outlet 290a. The door 280 may be rotatably coupled to the air blowing unit 190. The door 280 may be rotatably coupled to the guide panel 270 or the shroud panel 260 of the air blowing unit 190. In this embodiment, the door 280 is rotatably coupled to the guide panel 270. The door 280 may partially slide on a front surface of the guide panel 270 to open and close the guide hole 270a. Further, the door 280 may partially slide on a rear surface of the main body front panel 290 to open and close the outlet 290a. That is, the door 280 may partially slide between the guide panel 270 and the main body front panel 290 to open and close the guide hole 270a and the outlet 290a concurrently.

The base front panel 220 may form a lower front appearance of the air conditioner. The base front panel 220 may cover the open front of the base rear panel 210 coupled to the connector 230. The base front panel 220 may be implemented as a curved plate. The base front panel 220 may be coupled to the connector 230 at the rear of the base front panel 220, and the base front panel 220 may be coupled to the main body front panel 290 at a top of the base front panel 220.

The main body front panel 290 may form an upper front appearance of the air conditioner. The main body front panel 290 may have the air outlet 290a to discharge the air passing through guide hole 270a using the air blowing module 240. The outlet 290a may correspond to the guide hole 270a in terms of a shape. In this embodiment, the outlets 290a may be two as the two guide holes 270a are defined. The two outlets 290a may be define at both lateral sides relative to the central line C. Each air outlet 290a may be vertically elongated. Each outlet 290a may be bent toward the central line C at upper and lower portions thereof. Each outlet 290a may taper from a middle point to top and bottom points thereof, respectively. The outlet 290a may be opened and closed by the door 280.

The main body front panel 290 may be implemented as a curved plate. The main body front panel 290 may be coupled, at a bottom thereof, to the base front panel 220, and may be coupled, at a side portion thereof, to the main body rear panel 250. The main body front panel 290 may have an input/output hole 290b to partially expose an input/output module 300. The input/output hole 290b may have a circular form.

The input/output module 300 may be configured to receive a user command or display an operation state of the air conditioner. The input/output module 300 may be coupled to the main body front panel 290 at a rear of the panel 290 to be partially exposed through the input/output hole 290b to the outside.

The air conditioner may be applied to the wall-mounted air conditioner, and/or stand-type air conditioner. Hereinafter, for the sake of the convenience, a reference will be made to the wall-mounted air conditioner.

Figure 7:
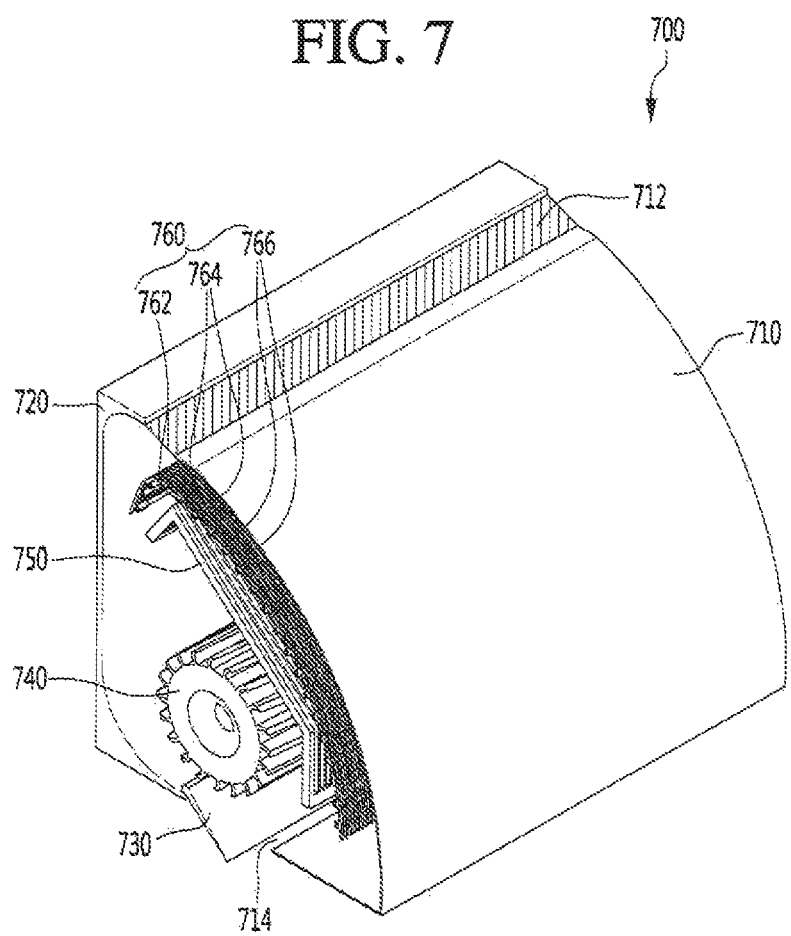
FIG. 7 is a partially cut-away perspective view of an air conditioner according to another embodiment.

FIG. 7 is a partially cut-away perspective view of an air conditioner according to another embodiment. As shown in FIG. 7, the air conditioner in accordance with this embodiment may include a UV sterilization module 760 provided in a main body 700. The UV sterilization module 760 may include a porous main body 762 and a UV lamp 764.

In this embodiment, the main body 700 may include a front panel 710, and a chassis 720. The main body 700 may receive a wind-direction adjustment member or adjuster 730, a fan 740, a heat exchanger 750, the porous main body 762, and the UV lamp 764. As shown in FIG. 7, the air conditioner may include all of the components as described with reference to FIGS. 1 to 4 in addition to the front panel 710, the chassis 720, the wind-direction adjustment member 730, the fan 740, and the heat exchanger 750. With reference to FIG. 7, only the front panel 710, the chassis 720, the wind-direction adjustment member 730, the fan 740, the heat exchanger 750, and the UV sterilization module 760 will be shown and described.

The main body 700 may have an air inlet 712 defined in a top thereof and an air outlet 714 defined in a bottom of thereof. The front panel 710 may define a front portion of the air conditioner. The main body 700 may have the air inlet 712 defined in a top of the air conditioner and the air outlet 714 defined in a bottom of the air conditioner.

The front panel 710 may form a front appearance of the air conditioner, and may be configured to pivot around a top portion thereof to maintain inner components of the air conditioner. Further, in this embodiment, the front panel 710, the chassis 720, the wind-direction adjustment member 730, the fan 740, and the heat exchanger 750 may have the same configurations and functions as described with reference to FIGS. 1 to 4.

In this embodiment, the UV sterilization module 760 may be disposed or provided upstream of the heat exchanger 750 in terms of an air flow path. The UV sterilization module 760 may be disposed or provided in the air suction channel between the front panel 710 and the heat exchanger 750.

The porous main body 762 may be configured to allow passage of air therethrough. The porous main body 762 may have holes 766 formed therein. For example, the porous main body 762 may be implemented as a porous plate having the holes 766 formed therein. Alternatively, the porous main body 762 may be implemented as a mesh of wires wherein the holes 766 may be defined between the wires. Hereinafter, the porous main body 762 may be referred to as a mesh, a web, a main body, a body, a support body, a porous lamp support body, a web main body, a mesh body, or a web body, for example.

The porous main body 762 may have the holes 766 to guide the air to the UV lamp 764. Each hole 766 may have a size larger than or equal to a predetermined size to minimize a channel resistance due to the porous main body 762. Further, the porous main body 762 may be made of an elastic material. The porous main body 762 may have a round surface that conforms to a shape of the heat exchanger 750 or may have at least one curve. The porous main body 762 may be disposed or provided between the main body 700 and the heat exchanger 750.

The UV sterilization module 760 may emit heat using the UV lamp 764. The porous main body 762 may be made of a heat-resistance material. Further, the porous main body 762 may be made of a metal material rather than a plastic material. The porous main body 762 may be made of a material endurable against heat and humidity. For example, the porous main body 762 may be made of aluminum. The aluminum Al may include a pure aluminum and an aluminum alloy.

The porous main body 762 may be disposed or provided upstream of the UV lamp 764 and the heat exchanger 750 in terms of an air flow path. The porous main body 762 may have a photocatalyst coating formed thereon. Thus, the air may be deodorized using the porous main body 762 and then may move to the UV lamp 764 and the heat exchanger 750. That is, when the porous main body 762 has a photocatalyst coating formed thereon, an odorized substance in the air may be minimally or hardly attached to the UV lamp 764. When the odorized substance is attached on the UV lamp 764, the UV lamp 764 may be deteriorated.

For example, the photocatalyst coating may include a $TiO_2$, $ZnO$, $CdS$, $ZrO_2$, $V_2O_3$, or $WO_2$ coating. The air that flows into the air inlet 712 may be deodorized using the porous main body 762, and then, may be sterilized using the UV lamp 764. Thus, the deodorized and sterilized air may be passed to the heat exchanger 750.

The porous main body 762 may be configured to allow a minimum air flow interference in the air flow channel. Further, while the air passes through the porous main body 762, the air may flow adjacently to the UV lamp 764. Thus, the air may receive a strong UV intensity. This may lead to improvement in sterilization by the UV sterilization module 760.

The UV sterilization module 760 may include a plurality of the UV lamp 764. Thus, the plurality of UV lamps 764 may be spaced from each other. The plurality of UV lamps 764 may be at least partially arranged in a series manner. The plurality of UV lamps 764 may be entirely arranged in a series manner. The plurality of UV lamps 764 may have a predetermined spacing between them. The plurality of UV lamps 764 may be at least partially arranged in a parallel manner. The plurality of UV lamps 764 may be entirely arranged in a parallel manner.

The plurality of UV lamps 764 may be spaced from the porous main body 762. The plurality of UV lamps 764 may be at least partially disposed or provided between the porous main body 762 and the heat exchanger 750. Further, some of the plurality of UV lamps 764 may be disposed or provided between the porous main body 762 and the heat exchanger 750, while the other of the plurality of UV lamps 764 may be disposed or provided between the porous main body 762 and front panel 710. The UV lamps 764 between the porous main body 762 and front panel 710 may sterilize the air passing between the air inlet 712 and porous main body 762. Subsequently, the UV lamps 764 between the porous main body 762 and the heat exchanger 750 may sterilize the air passing through the porous main body 762.

As described above, the UV lamps may be distributed across the porous main body 762, and the porous main body 762 may have the photocatalyst coating. Thus, the air may be sterilized, a first time, between the air inlet 712 and porous main body 762. Subsequently, the air may be deodorized using the porous main body 762, and then, the air may be sterilized, a second time, between the porous main body 762 and the heat exchanger 750.

The UV sterilization module 760 may include one or more holder (not shown) to support the UV lamp 764. The holder may support the UV lamp 764 such that the UV lamp 764 is spaced from the porous main body 762. A plurality of holders may support the UV lamps 764 respectively. A pair of the holders may support a single UV lamp 764. The UV sterilization module 760 may include a plurality of pairs of the holders. The plurality of pairs of the holders may be spaced from each other.

In one embodiment, the UV sterilization module 760 may include a plurality of UV lamps 764, a power supply (not shown), and an electrical line (not shown). The UV lamp 764 may be implemented as an external electrode type. Therefore, the UV lamp 764 may have a first electrode at one or a first side thereof, and a second electrode at the other or second side thereof. The first electrode and the second electrode may be formed by coating a conductive solder liquid from an outside of the UV lamp 764. Further, the first electrode and second electrode may be formed by coating a silver paste. Furthermore, the first electrode and second electrode may be formed by applying a carbon-nano tube and curing it. That is, the UV lamp 764 and the first electrode and the second electrode may be individually formed. Thus, an electric field may be generated between the first electrode and the second electrode. Then, the electric field may electrically discharge an emission material in the UV lamp 764 to generate UV rays. As the material enclosed in the UV lamp 764 does not contact the first electrode and the second electrode, the UV lamp 764 may have a less amount of heat, to increase a life span of the UV lamp 764.

The power supply may supply power to the UV lamp 764. The power supply may stabilize a current to be supplied to the UV lamp 764. Further, the power supply may generate a high voltage required to generate UV rays in the UV lamp 764. That is, the power supply may be configured to change an output frequency and drive voltage based on a drive frequency and drive voltage for driving the plurality of UV lamps 764. For example, the power supply may act as an inverter, and a stabilizer, for example.

The electric line may connect the power supply and the plurality of UV lamps 764. To be specific, the electric line may connect the first electrode and the second electrode and the power supply. Further, the electric line may realize a parallel connection between the plurality of UV lamps 764 and the power supply. That is, the parallel connection between the power supply and the plurality of UV lamps 764 may allow the plurality of UV lamps 764 to turn on concurrently. Further, when the plurality of UV lamps 764 includes a defective UV lamp, the defective UV lamp may be simply replaced.

Although the UV lamp 764 has been described as an external electrode fluorescent lamp, embodiments are not limited thereto. The electrodes may be disposed or provided within the UV lamp.

Hereinafter, a configuration of the UV lamp 764 will be described. The UV lamp 764 as an external electrode fluorescent lamp may be formed in a hollow bar or tube shape. Further, the UV lamp 764 may have a sealed inner space. The UV lamp 764 may be made of quartz or borosilicate or a glass containing quartz or borosilicate. Further, the UV lamp 764 may have an emission material enclosed therein to generate the UV rays. The emission material may be discharged via an electric field generated between the first electrode and the second electrode at both ends of the UV lamp 764 respectively to generate the UV rays.

For example, the emission material may include at least one of Hg, Ne, Xe, Kr, Ar, XeBr, XeCl, KrBr, KrCl, or $CH_4$. Further, except for Hg, all of the emission materials may be present in a gas state. Further, the emission material may be enclosed in the UV lamp 764 under a constant pressure. For example, the emission material may be enclosed in the UV lamp 764 under an upper or middle pressure. The UV lamp 764 may have a small diameter to facilitate an installation of the lamp in the air conditioner. For example, the UV lamp 764 may have a diameter of about 1 mm to about 7 mm.

When the UV lamp 764 has a diameter below about 1 mm, the lamp may be damaged and filling of the emission material may be not easy. When the UV lamp 764 has a diameter above about 7 mm, air flow resistance due to the lamp may increase. Further, a voltage to discharge the emission material in the UV lamp 764 may increase, thereby increasing power consumption.

The UV lamp 764 may be oriented horizontally in the air conditioner. The UV lamp 764 may be oriented horizontally length-wise. Further, the UV lamp 764 may have a thickness to withstand an inner pressure of the gas enclosed in the UV lamp 764. For example, the UV lamp 764 may have a thickness of about 0.2 mm to about 2 mm. The diameter, length, and thickness of the UV lamp 764 may be not limited to the above dimensions.

The UV lamp 764 may have the first electrode and the second electrode externally disposed or provided at both sides of the UV lamp 764, respectively. Further, the first electrode and the second electrode may be made of a conductive solder liquid at both sides of the UV lamp 764, respectively. Further, the first electrode and the second electrode may be formed by applying a silver paste. Further, the first electrode and the second electrode may be formed by applying and curing a carbon nano-tube (CNT). For example, the UV lamp 764 may be immersed, at both ends thereof, into the conductive solder liquid, and the conductive solder liquid may be cured to form the first electrode and the second electrode.

That is, an outer surface of the UV lamp 764 may dip into the conductive solder liquid, thereby to simplify a manufacturing process thereof. Further, conductive material and conductive solder liquid may include one or more of Ag, carbon nano-tube (CNT), Cu, and Pt. Thus, each of the first electrode and the second electrode may extend from both ends of the UV lamp 764 in a lengthwise direction of the UV lamp 764. Further, each of the first electrode and the second electrode may have a length of at least about 1 cm to about 3 cm from both ends of the UV lamp 764.

When each of the first electrode and the second electrode has a length below about 1 cm, it may be difficult to discharge the emission material in the UV lamp 764. That is, the first electrode and the second electrode may have a small area lowering a discharge efficiency of the emission material. When each of the first electrode and the second electrode has a length above about 3 cm, it may not be difficult to discharge the emission material in the UV lamp 764, but the UV emission area may be smaller due to a smaller area of the first electrode and the second electrode.

The UV sterilization module 760 may sterilize a harmful substance in the air using a parallel connection of the plurality of UV lamps 764 disposed or provided on the porous main body 762, which the air having flowed into the air inlet 712 passes through the porous main body 762 toward the heat exchanger 750. The UV lamp 764 may generate UV rays having a wavelength of about 250 nm to about 260 nm with a strong sterilization against a microorganism. The wavelength of about 250 nm to about 260 nm may have a sterilization effect 1000 to 10000 times larger than a sterilization effect of a near UV.

When the UV ray is irradiated into a DNA of a microorganism, a molecular structure of thymine among bases of the DNA may be intensively destroyed. Thymine absorbing the UV rays may be attached to adjacent thymine or cytosine. Thus, the thymine may be polymerized to stop the replication of DNA. Further, UV rays oxidize phospholipids and proteins forming a cell membrane to suppress life activity of bacteria.

The UV sterilization module 760 may be installed or provided in various locations in the air conditioner. For example, the UV sterilization module 760 may be located between the front panel 710 and the front frame (not shown) of the air conditioner. That is, the porous main body 762 may be coupled to the front panel 710 at a rear of the panel 710 to direct the UV lamp 764 toward the heat exchanger 750.

Further, the UV sterilization module 760 may be located between the front frame and the filter (not shown) of the air conditioner. That is, the porous main body 762 may be coupled to the front frame at a rear of the frame to direct the UV lamp 764 toward the heat exchanger 750.

Further, the UV sterilization module 760 may be located between the filter frame (not shown) and the heat exchanger 750 of the air conditioner. That is, the porous main body 762 may be coupled to the filter frame at a rear thereof to direct the UV lamp 764 toward the heat exchanger 750.

Figure 8:
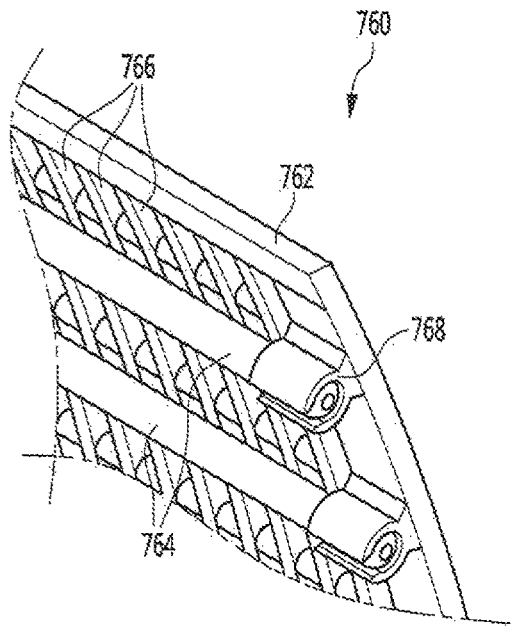
FIG. 8 is a partially enlarged perspective view of a UV sterilization module in the air conditioner according to another embodiment.

FIG. 8 is a partially enlarged perspective view of a UV sterilization module in the air conditioner according to another embodiment. As shown in FIG. 8, the UV sterilization module 760 may include porous main body 762, UV lamp 764, holes 766, and holder(s) 768.

In one embodiment, the UV sterilization module 760 may have holes 766 formed in a polygonal, circular, and/or an elliptical shape. Further, a variation of size of the holes 766 may lead to adjustment of a flow rate of an air passing through the porous main body 762.

The porous main body 762 may have one or more holder 768 at a front thereof. A plurality of the holder 768 may be arranged to be spaced from each other. Further, the porous main body 762 may have a plurality of holders 768 on each of both sides thereof. Each of the plurality of holders 768 may be made of a metal, and may be structured to surround the UV lamp 764.

Further, the porous main body 762 may have holders 768 on one side thereof where the holders 768 may be spaced from each other. The UV lamp 764 may be fitted into the holders 768 at both ends of the UV lamp respectively. Further, the porous main body 762 may have holders 768 arranged at a left, middle, and right points respectively on one side thereof. The UV lamp 764 may be fitted into the holders 768 at the left, middle, and right portions of the UV lamp, respectively.

The porous main body 762 may have a waterproof sealing or seal (not shown) around the holder 768 to prevent corrosion, for example, of the electrodes and holder 768 of the UV lamp 764. Further, although not shown in FIG. 8, the UV sterilization module 760 may include a metal rail (not shown) provided on the porous main body 762. The metal rail may be electrically connected to the holder 768, and thus, current may flow through the metal rail and the holder 768 to the UV lamp 764. The metal rail may be connected to the plurality of holders 768, and thus, the current applied to the metal rail may flow to the plurality of holders 768. The metal rail may act as a parallel connector to realize a parallel connection of the plurality of UV lamps 764. The metal rail may be referred to as a bus bar.

The plurality of holders 768 may be arranged to be spaced from each other on one surface of the metal rail. That is, the plurality of holders 768 may be arranged on the metal rail at a predetermined distance. A water-proof sealing or seal may be provided to cover not only the electrode, and holder 768 of the UV lamp 764 but also the metal rail.

Figure 9A:
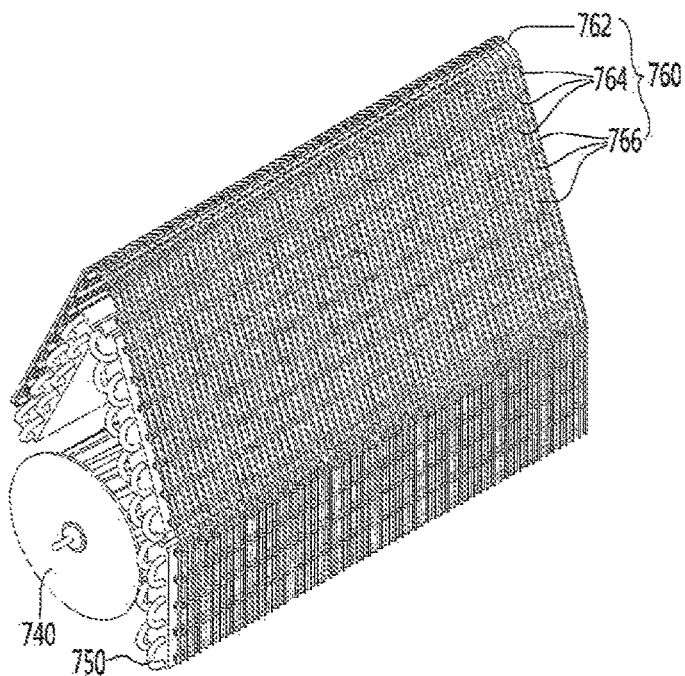
FIGS. 9A-9B are perspective views illustrating positions of a UV sterilization module, a heat exchanger, and a fan in an air conditioner according to an embodiment.
Figure 9B:
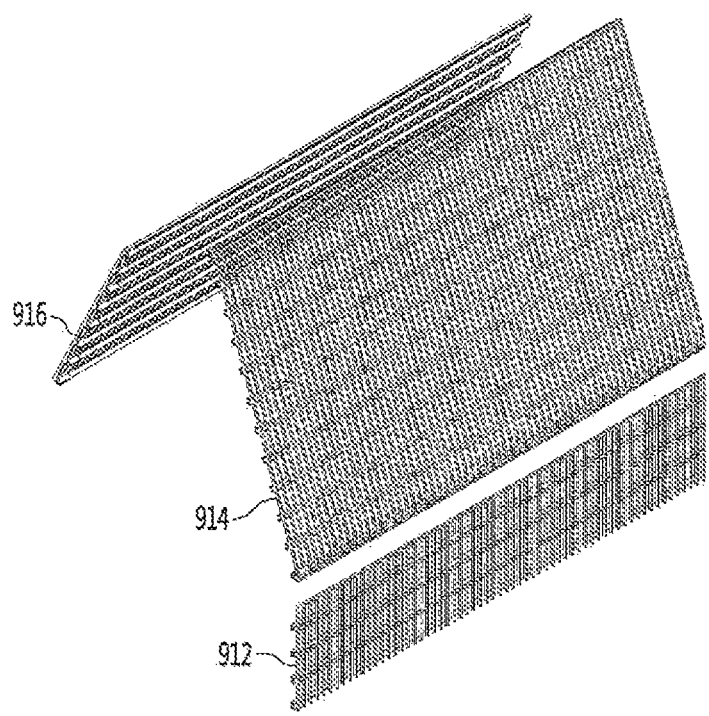

FIGS. 9A-9B are perspective views illustrating positions of a UV sterilization module, a heat exchanger, and a fan in an air conditioner according to an embodiment. As shown in FIGS. 9A-9B, in one embodiment, the air conditioner may include the UV sterilization module 760 including the porous main body 762, the UV lamp 764, the heat exchanger 750, and the fan 740. The UV sterilization module 760 may include the porous main body 762 with holes 766 having a size larger than or equal to a predetermined size so as not to interfere with the air flow.

The UV sterilization module 760 may have the porous main body 762 made of an elastic material. The porous main body 762 may be curved in a conformal manner to a shape of the heat exchanger 750. The UV sterilization module 760 may include a plurality of UV lamps 764. The plurality of UV lamps 764 may be arranged to be spaced from each other on the porous main body 762 in a parallel fashion. The porous main body 762 may include a holder (not shown) to support the UV lamp 764. The UV lamps 764 may be fitted into the holders respectively arranged on the porous main body 762 to be spaced from each other. The UV sterilization module 760 may sterilize a harmful substance in the air using a parallel connection of the plurality of UV lamps 764 disposed or provided on the porous main body 762 while the air having flowed into the air inlet 712 passes through the porous main body 762 toward the heat exchanger 750.

As described above, the porous main body 762 may be made of an elastic material to cover an entire area of the heat exchanger 750. The porous main body 762 may conform to the heat exchanger 750 in shape, and thus, may be coupled to the heat exchanger 750. The porous main body 762 may have a bent portion to realize a conformal registering of the porous main body 762 on the heat exchanger 750. Further, the porous main body 762 may include a first porous main body 912 corresponding to a first or vertical portion of the heat exchanger 750, a second porous main body 914 corresponding to a second or front tilted portion of the heat exchanger 750, and a third porous main body 916 corresponding to a third or rear tilted portion of the heat exchanger 750. Further, although not shown in FIG. 9, in one embodiment, the porous main body of the UV sterilization module 760 may vary in a size and shape depending on a size and shape of the UV lamp.

Figure 10A:
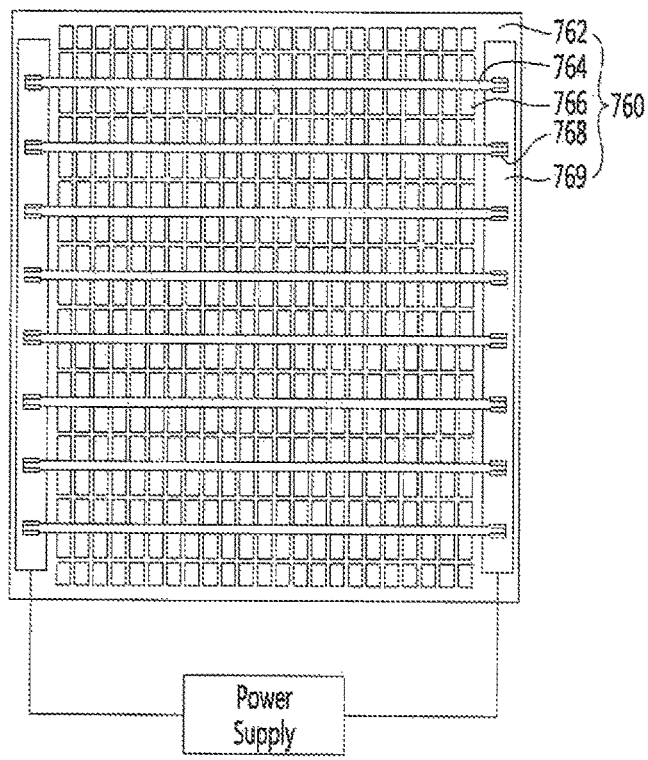
FIGS. 10A-10B show an example of a UV sterilization module according to an embodiment having metal rails.
Figure 10B:
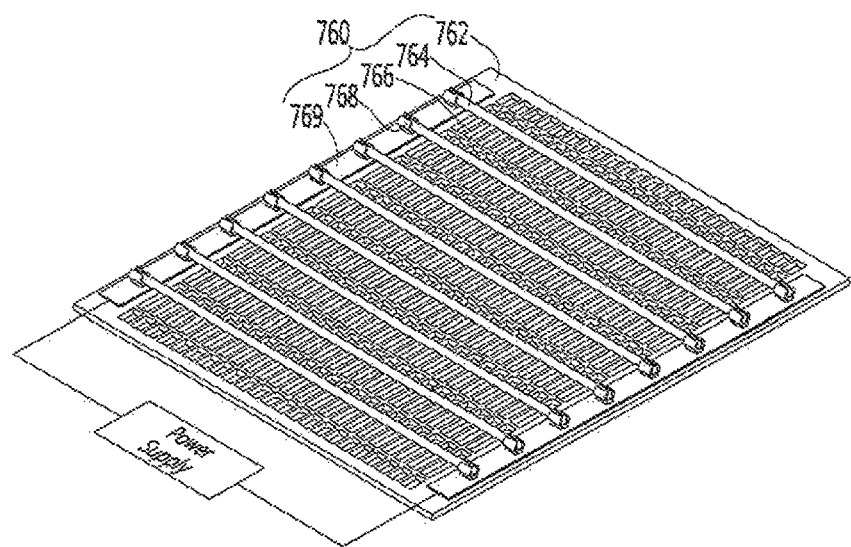

FIGS. 10A-10B show an example of a UV sterilization module according to an embodiment having metal rails. As shown in FIGS. 10A-10B, in one embodiment, the UV sterilization module 760 may include porous main body 762, a plurality of UV lamps 764, a plurality of holes 766, a plurality of holders 768, and metal rails 769.

The porous main body 762 may have the plurality of holes 766 to receive air. The air into the plurality of holes 766 may be sterilized using the plurality of UV lamps 764. The metal rails 769 may be provided at first and second or left and right sides of the porous main body 762, respectively, with a given length. The plurality of holders 768 may be arranged to be spaced from each other on the metal rails 769. Thus, the plurality of holders 768 may be disposed or provided on first and second or left and right portions of the porous main body 762. Each of the plurality of UV lamps 764 may be fitted or provided with a pair of holders at the left and right portions of the porous main body, respectively.

In one embodiment, the UV sterilization module 760 may receive power from a power supply. Each UV lamp 764 may receive power via the electric line. Further, the holder 768 may be made of a metal, and the holder 768 may be connected to the electric line to supply power to each UV lamp. Further, employing the plurality of UV lamps 764 as the external electrode UV lamp may allow an easy power supply. That is, when the plurality of metal holders 768 and metal rails 769 are disposed and both metal rails 769 receive the power, all UV lamps 764 may receive the power concurrently. In this way, using the metal rails, UV lamp mounting and power supply may be facilitated.

Figure 11A:
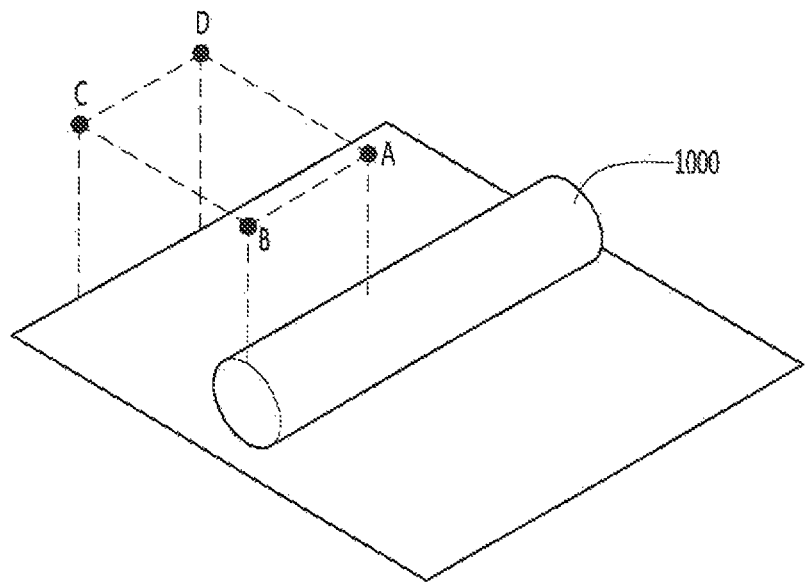
FIGS. 11A-11B are diagrams for describing power energies measured in a given region when a single related art UV lamp is employed.
Figure 11B:
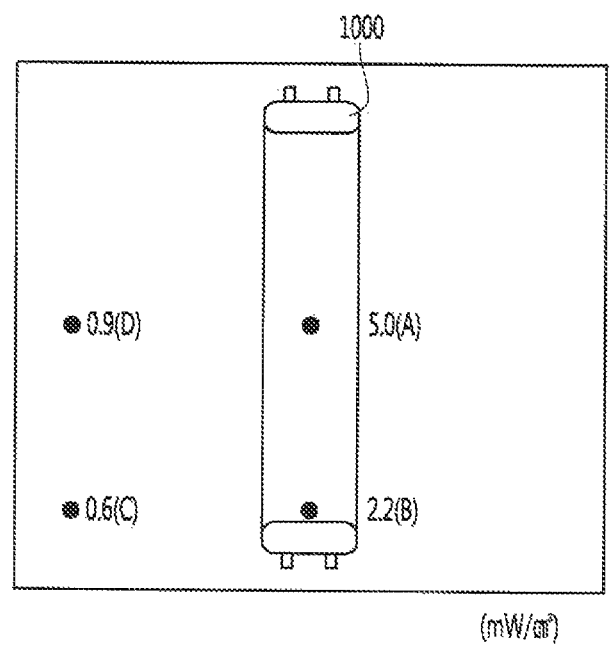
Figure 12A:
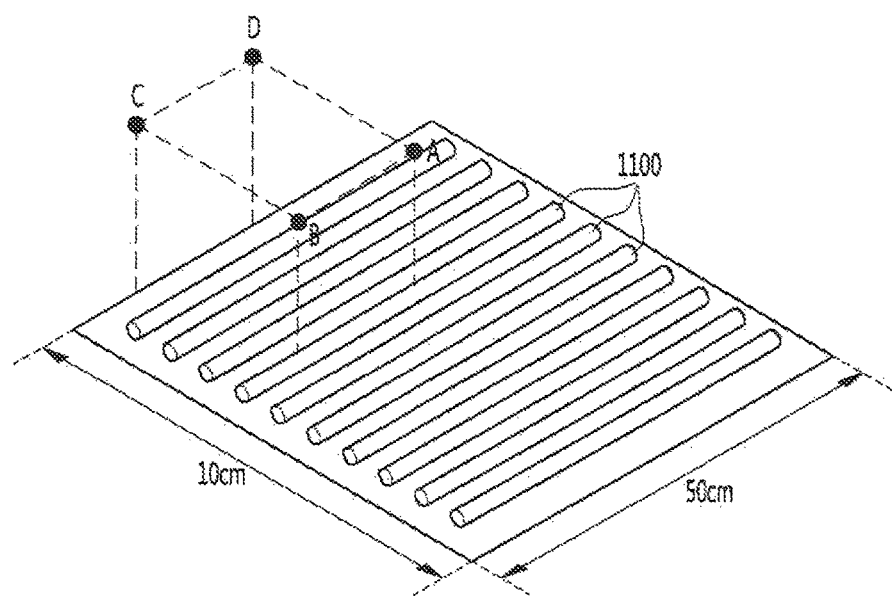
FIGS. 12A-12B are diagrams for describing power energies measured in a given region when a parallel combination of multiple UV lamps according to an embodiment is employed.
Figure 12B:
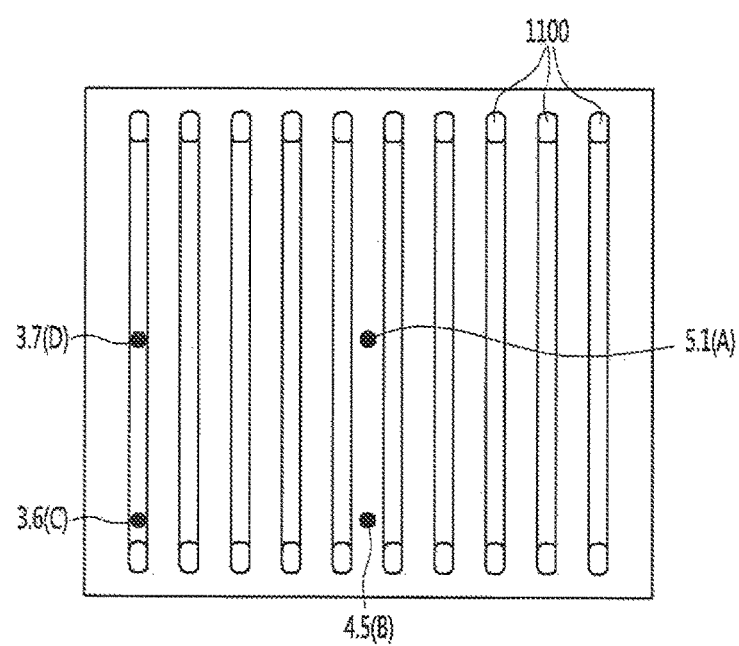

FIGS. 11A-11B are diagrams for describing power energies measured in a given region when a single conventional UV lamp is employed. FIGS. 12A-12B are diagram for describing power energies measured in a given region when a parallel combination of multiple UV lamps according to an embodiment is employed.

In FIGS. 11A-11B, a single related art UV lamp 1000 may be used to conduct UV sterilization, while in FIGS. 12A-12B, in one embodiment, a parallel connection of ten UV lamps 1100 may be used to conduct UV sterilization.

As shown in FIGS. 11A-11B, when the single related art UV lamp 1000 or is employed works, power energy measured in an A region amounts to about 5 m W/cm$^2$; power energy measured in a B region amounts to about 2.2 mW/cm$^2$; power energy measured in a C region amounts to about 0.6 mW/cm$^2$; and power energy measured in a D region amounts to about 0.9 mW/cm$^2$. As shown in FIGS. 12A-12B, in the one embodiment, when the ten UV lamps 1100 work, or are employed power energy measured in an A region amounts to about 5.1 W/cm$^2$; power energy measured in a B region amounts to about 4.5 mW/cm²; power energy measured in a C region amounts to about 3.6 mW/cm²; and power energy measured in a D region amounts to about 3.7 mW/cm².

That is, in the one embodiment, a plurality of the UV lamps 1100 with small diameters respectively works concurrently, a high power density may be achieved due to a small spacing between the lamps, and thus, an overlapping effect may occur. In contrast, a lower power density may be achieved due to a larger spacing between the lamps, and thus, a reduced overlapping effect may occur.

Thus, an approach where the single related art UV lamp 1000 works may have a larger power consumption than the present approach where the present ten UV lamps 1100 work concurrently. Therefore, taking into account power consumption, a space efficiency, and UV sterilization, using the plurality of the UV lamps 1100 in the one embodiment may be more effective than using the single related art UV lamp.

Figure 13:
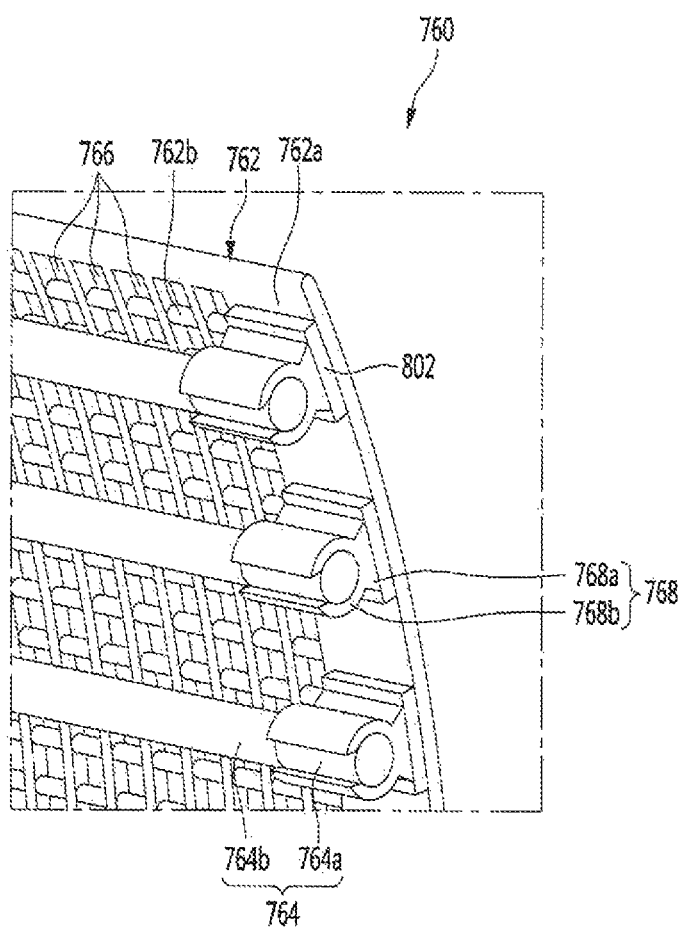
FIG. 13 is a diagram for describing a UV sterilization module according to an embodiment.
Figure 14:
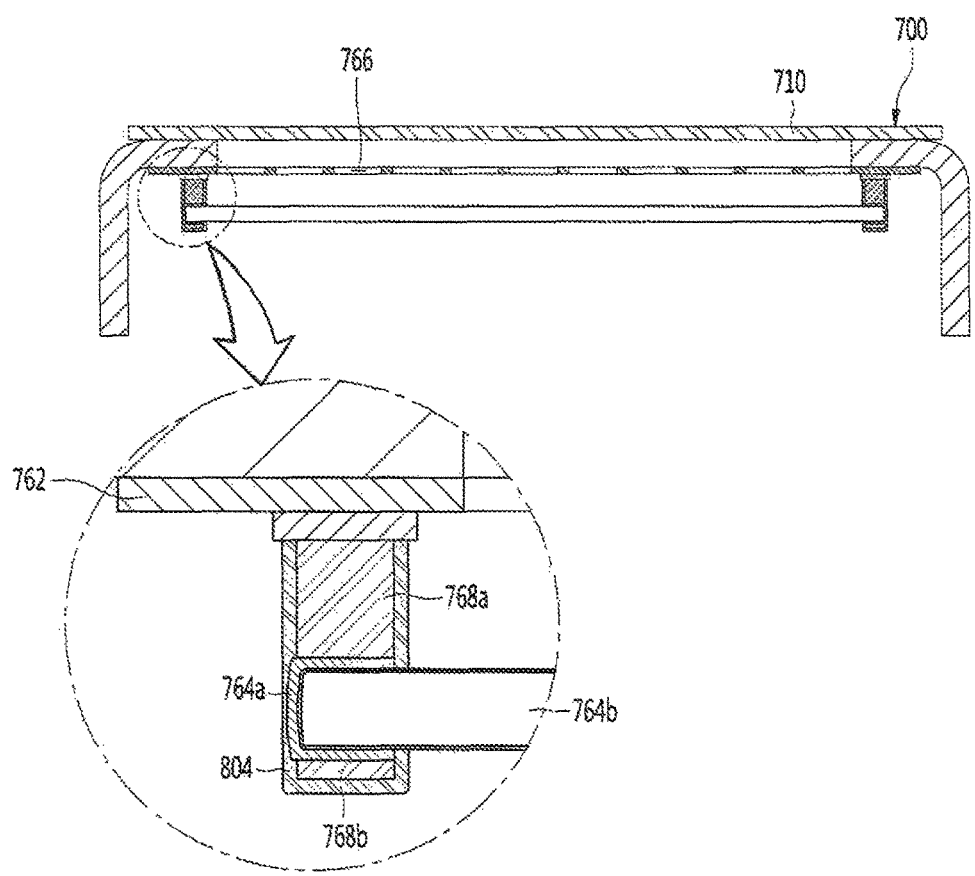
FIG. 14 is a vertical cross-sectional view of an air conditioner including a UV sterilization module according to another embodiment.
Figure 15:
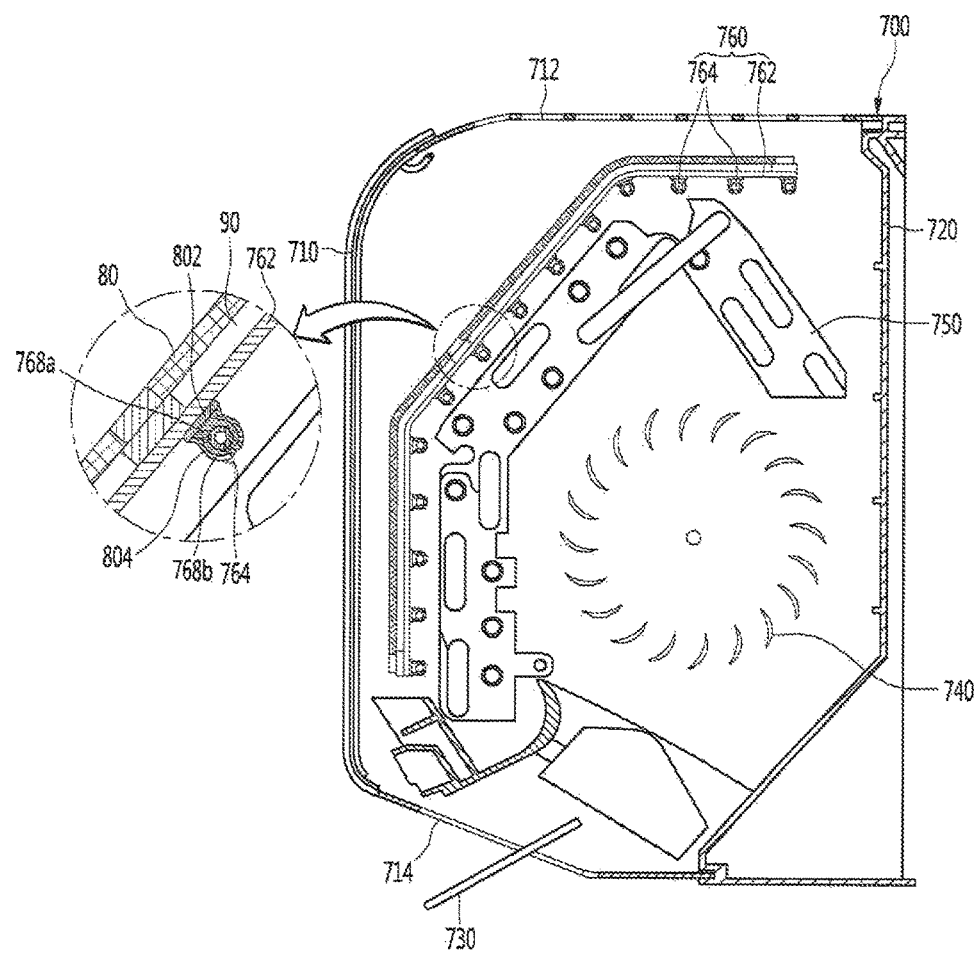
FIG. 15 is a horizontal cross-sectional view of the air conditioner of FIG. 14.

FIG. 13 is a diagram for describing a UV sterilization module according to an embodiment. FIG. 14 is a vertical cross-sectional view of an air conditioner including a UV sterilization module according to another embodiment. FIG. 15 is a horizontal cross-sectional view of the air conditioner of FIG. 14.

The UV sterilization modules 760 according to the embodiments of FIGS. 13 and 14 are identical to each other, except for a configuration of a sealing or seal 804. Thus, configurations and operations except for the sealing 804 will be simultaneously described. Further, description of the same configurations and operations as those described above have been omitted, and the following descriptions will focus on differences.

Referring to FIGS. 13 to 15, each of the UV sterilization modules 760 according to the embodiments of FIGS. 13 and 14 may include porous main body 762, UV lamp 764, a plurality of holes 766 provided in the porous main body 762, an insulating member or insulator 802, and holder 768. The porous main body 762 may be a conductor. The porous main body 762 may include a mounting portion 762a and an air hole portion 762b. The air hole portion 762b may have a plurality of the holes 766 to allow air to pass therethrough. The air hole portion 762 may have a plurality of the holes 766 which allow air to pass through and onto which UV rays emitted by the UV lamp are radiated.

The insulating member 802 may be provided in the mounting portion 762a. In a case where the UV sterilization module 760 does not include the insulating member 802, the holder 768 may be provided in the mounting portion 762a.

The mounting portion 762a may provide a path through which power supplied to the UV lamp 764 may pass. In the porous main body 762, the mounting portion 762a may be a conductor and the air hole portion 762b may be an insulator.

The mounting portion 762a and the air hole portion 762b may be integrally formed. The mounting portion 762a may not be included in the porous main body 762, and the insulating member 802 or the holder 768 may be provided in the air hole portion 762b.

The mounting portion 762a may be formed at both edge regions or portions of the porous main body 762. For example, the mounting portion 762a may be formed at first and second or left and right edge portions of the porous main body 762.

As the UV lamp 764 corresponding to the mounting portion 762a cannot radiate UV rays toward the porous main body 762 due to the holder 768, the hole 766 may not be formed in the mounting portion 762a. Therefore, in a case where the mounting portion 762a is included in the porous main body 762, a manufacturing cost may be reduced, as compared with a case where the entire porous main body 762 is manufactured as the air hole portion 762b.

The UV lamp 764 may be arranged to be spaced from the porous main body 762. The porous main body 762 may be formed to be longer in a first direction being a lengthwise direction of the UV lamp 764 than in a second direction perpendicular to the first direction. More specifically, when the UV lamp 764 is arranged in a transverse direction with respect to the porous main body 762, the porous main body 762 may be formed to be longer in a transverse direction than a longitudinal direction.

As air passing through the holes 766 formed in the air hole portion 762b of the porous main body 762 may be sterilized by the UV lamp 764, the UV lamp 764 may be arranged to face the air hole portion 762b. That is, the UV lamp 764 may be disposed or provided to correspond to the air hole portion 762b.

The UV lamp 764 may include external electrodes 764a and a lamp main body 764b. The external electrodes 764a may be, respectively, provided on both ends of the lamp main body 764b. The external electrodes 764a may be a first electrode and a second electrode.

The UV sterilization module 760 may be connected to a power supply, such as an inverter, via an electrical line. When a voltage is applied between the external electrodes 764a of both ends of the UV lamp 764 by the inverter and the electrical line, UV rays may be radiated from the lamp main body 764b. The UV rays radiated by the lamp main body 764b may sterilize air passing therethrough or along a surface of the heat exchanger 750 and the UV sterilization module 760.

The UV sterilization module 760 may include a plurality of the UV lamps 764, and the plurality of UV lamps 764 may be arranged to be spaced from each other. The plurality of UV lamps 764 may be arranged in parallel at preset or predetermined intervals. The plurality of UV lamps 764 may be arranged side by side.

The UV sterilization module 760 may include the holder 768 to support the UV lamp 764. More specifically, the UV sterilization module 760 may include a plurality of pairs of the holder 768 arranged to be spaced from each other on one surface of the porous main body 762.

The holder 768 may be made of a metal material. The holder 768 may be a conductive holder through which electricity is conducted.

The holder 768 may include a main body 768a, and a lamp coupling portion 768b that extends from the main body 768a and supports the UV lamp 764.

Each of the holders 768 may support the UV lamp 764 such that the UV lamp 764 is spaced from the porous main body 762. The UV lamp 764 may be supported by one pair of holders 768.

The external electrode 764a of the UV lamp 764 may be connected to the holder 768, and one pair of holders 768 may be, respectively, connected to the external electrodes 764a of both ends of the UV lamp 764. The lamp coupling portion 768b of the holder 768 may surround the UV lamp 764 and at least a portion of the external electrode 764a.

In this case, the holder 768 may be electrically connected to the external electrode 764a of the UV lamp 764. More specifically, one pair of holders 768 supporting the external electrodes 764a of both ends of the UV lamp 764 may be connected to the power supply, such as the inverter, through the electrical line. As the one pair of holders 768 may be electrically connected to the external electrodes 764a of both ends of the UV lamp 764, respectively, a voltage may be applied between the external electrodes 764a of both ends of the UV lamp 764, and thus, the UV lamp 764 may be operated.

The UV sterilization module 760 may include the insulating member 802 so as to prevent electricity from being conducted between the porous main body 762 and the holder 768. The insulating member 802 may be provided in the mounting portion 762a of the porous main body 762. The insulating member 802 may be a material, such as rubber, and may be an elastic material.

The insulating member 802 may be provided between the holder 768 and the porous main body 762. One or a first surface of the insulating member 802 may contact the porous main body 762, and a second or the surface opposite to the one surface of the insulating member 802 may contact the holder 768. More specifically, the one surface of the insulating member 802 may contact the mounting portion 762a, and the surface opposite to the one surface of the insulating member 802 may contact the main body 768a.

In a case where the material of the porous main body 762 is a metal, such as aluminum, if the insulating member 802 is not provided, the current applied to the holder 768 flows through the porous main body 762, causing short circuit or discharge. Further, if the current applied to the holder 768 flows through the porous main body 762, a potential difference between the external electrodes 764a of both ends of the UV lamp 764 becomes zero, Thus, the UV lamp 764 may not operate.

An area of the insulating member 802 may be larger than an area of a top surface of the main body 768a of each of the holders 768. The top surface of the main body 768a may refer to a surface facing the porous main body 762 from the main body 768a.

The insulating member 802 may include a plurality of insulating members 802 which corresponds to each of the holders 768 and is spaced from each other. Further, the insulating member 802 may be a single insulating member disposed or provided between all the holders 768 and the porous main body 762. A size and number of insulating members 802 may be determined as necessary.

The plurality of UV lamps 764 may be disposed or provided between the porous main body 762 and the heat exchanger 750. A front surface of the porous main body 762 may face the heat exchanger 750.

The UV lamp 764 may be disposed or provided on a front surface of the porous main body 762. A rear surface of the porous main body 762 may face a filter frame 90 that supports the filter 80. The rear surface of the porous main body 762 may partially contact the filter frame 90 that supports the filter 80.

The filter 80 and the filter frame 90 may not be included in the air conditioner, and the porous main body 762 may serve as the filter 80. The UV lamp 764 may be disposed or provided on a surface opposite to the filter 80 with respect to the porous main body 762. The UV lamp 764 may be arranged to face the filter 80 from the porous main body 762.

Referring to FIGS. 14 and 15, the UV sterilization module 760 according to this embodiment may further include the water-proof sealing or seal 804 that surrounds the holder 768 and the external electrodes 764a of the UV lamp 764. The water-proof sealing 804 may surround both the holder 768 and the external electrodes 764a. The water-proof sealing 804 may further surround the insulating member 802.

The water-proof sealing 804 may prevent corrosion caused when the holder 768 and the external electrodes 764a of the UV lamp 764 to which the current is applied are exposed to external moisture or foreign substances, and may prevent occurrence of short circuit or discharge. The water-proof sealing 804 may be made of a thermosetting resin so as to prevent deformation or damage caused by heat emitted by the UV lamp 764.

For example, the water-proof sealing 804 may be made of at least one of a polyurethane resin, an epoxy resin, or a silicon rubber. The above-mentioned materials are precisely moldable because a weight change rate thereof is low during curing, and have excellent durability because the materials are neither distorted nor deformed even after curing.

Figure 16:
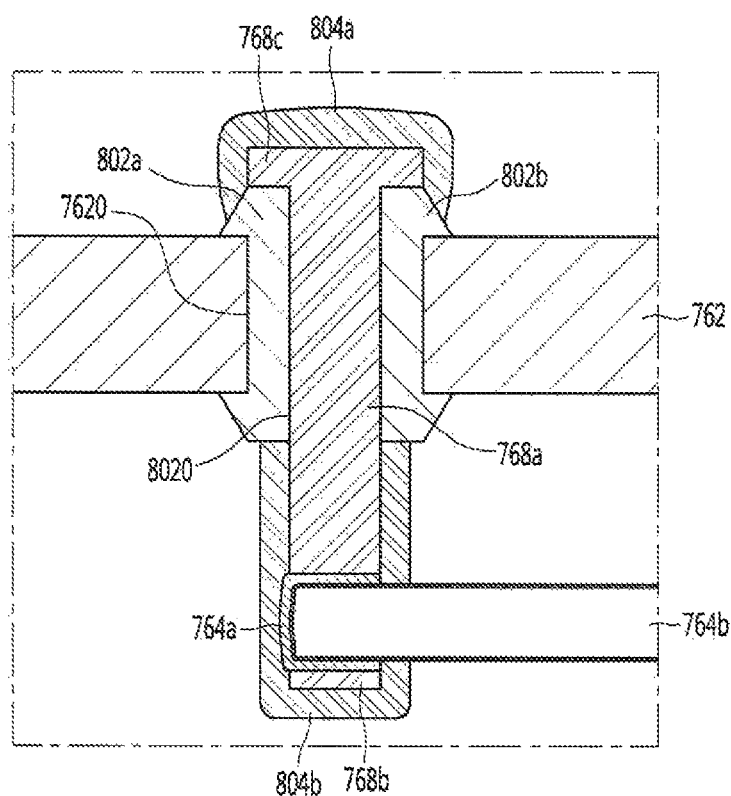
FIG. 16 is a vertical cross-sectional view for describing a UV sterilization module according to still another embodiment.
Figure 17:
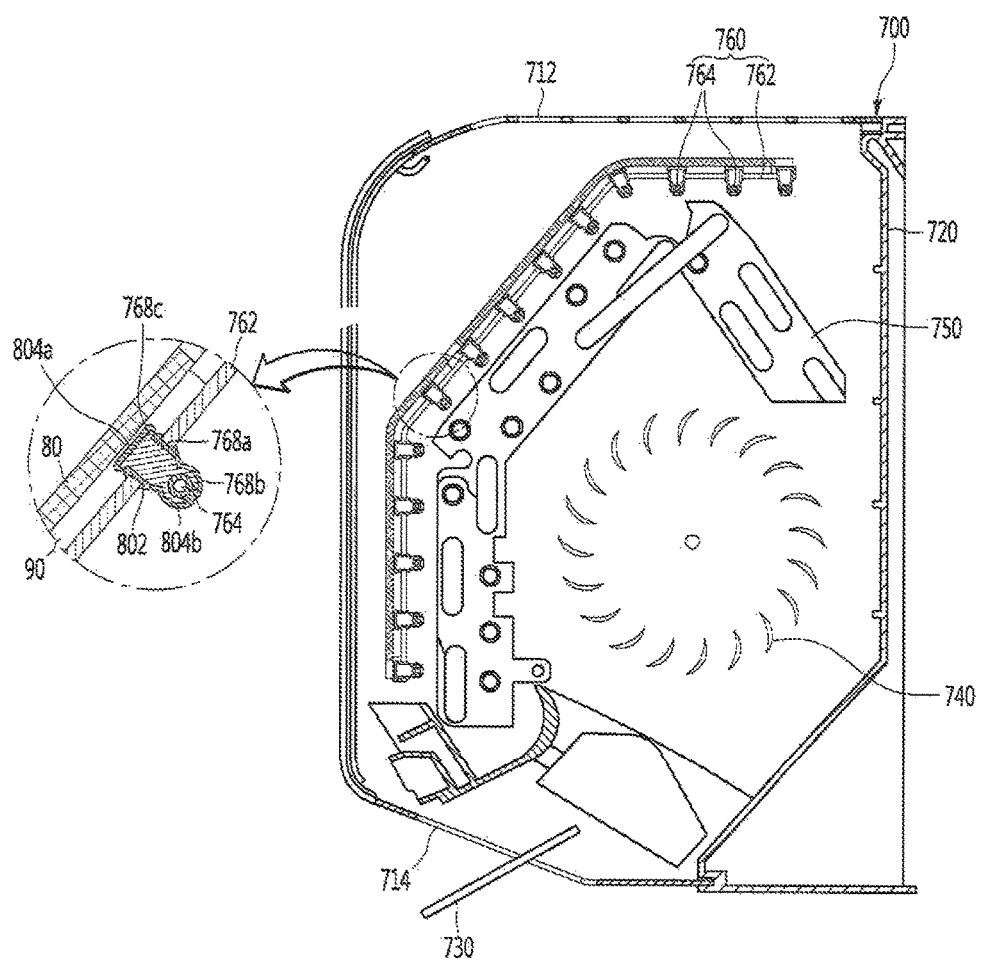
FIG. 17 is a horizontal cross-sectional view of an air conditioner including the UV sterilization module of FIG. 16.

FIG. 16 is a vertical cross-sectional view for describing a UV sterilization module according to still another embodiment. FIG. 17 is a horizontal cross-sectional view of an air conditioner including the UV sterilization module of FIG. 16. As the UV sterilization module according to this embodiment differs from the UV sterilization module according to the embodiment of FIGS. 14-15 in terms of shapes and configurations of holder 768, water-proof sealing 804, and insulating member 802, the following descriptions will focus on differences and redundant descriptions thereof have been omitted.

The insulating member 802 may be inserted into and connected to the hole 766 formed in the porous main body 762. Alternatively, an insertion hole 7620 may be formed in the porous main body 762 separately from the hole 766 for smooth air flow. The insulating member 802 may be inserted into and connected to the insertion hole 7620. Hereinafter, a case where the insulating member 802 is inserted into the separate insertion hole 7620 will be described by way of example.

The insertion hole 7620 may have various shapes according to shapes of the insulating member 802 and the holder 768. For example, when cross-sections of the insulating member 802 and the holder 768 have a rectangular shape, the insertion hole 7620 may also have a rectangular shape.

The insulating member 802 may include an insulating body 802a and a hook 802b. The insulating body 802a may have a hollow 8020 into which the main body 768a of the holder 768 may be inserted. The hook 802b may be formed in the insulating body 802a and may fix the insulating member 802 to the porous main body 762.

An outer peripheral surface of the insulating body 802a may contact an inner peripheral surface of the insertion hole 7620. For example, when the cross-section of the insulating body 802a and the shape of the insertion hole 7620 are circular, a diameter of the outer peripheral surface of the insulating body 802a may be equal to a diameter of the insertion hole 7620. The inner peripheral surface of the insulating body 802a may contact the main body 768a of the holder 768 inserted into the hollow 8020 formed in the insulating body 802a.

The hook 802b may extend outward from edges of both ends of the insulating body 802a. Alternatively, the hook 802b may extend outward from an edge of one end of the insulating body 802. Alternatively, the hook 802b may extend outward from a portion of both ends or one end of the insulating body 802.

The hook 802b may contact one surface or both surfaces of the porous main body 762. The hook 802b may prevent the insulating member 802 from being released from the insertion hole 7620.

As the insulating member 802 may be an elastic material, such as rubber, the hook 802b is less distorted than a diameter of the insertion hole 7620 in the process of inserting the insulating member 802 into the insertion hole 7620, and when the insulting member 802 is completely inserted into the insertion hole 7620, the insulating member 802 is returned to the original shape by the elasticity of the insulating member 802. Thus, the insulating member 802 may be fixed to the insertion hole 810.

The holder 768 may include main body 768a, lamp coupling portion 768b, and a fixing portion 768c. At least a portion of the main body 768a may be inserted into the hollow 8020 of the holder body 802a.

The lamp coupling portion 768b may be formed on one side of the main body 768a, and the UV lamp 764 may be coupled to the lamp coupling portion 768b. The fixing portion 768c may be formed on the other side of the main body 768a and may contact the insulating member 802.

The main body 768a may be inserted into the hollow 8020 formed in the Insulating body 802a. A portion of the main body 768a may be disposed or provided in the hollow 8020 formed in the insulating body 802a, and the other portion thereof may be disposed or provided at an outside of the insulating body 802a.

Alternatively, the entire main body 768a may be inserted into the hollow 8020 formed in the insulating body 802a. In this case, a distance between the UV lamp 764 and the porous main body 762 may be minimized.

A side surface of the main body 768a may partially contact an inner surface of the insulating body 802a. A portion of the main body 768a may be disposed or provided inside of the insulating body 802a, and the fixing portion 768c and the lamp coupling portion 768b may be disposed or provided outside of the insulating body 802a.

The fixing portion 768c may extend in a direction from an end to an edge of the main body 768a. The fixing portion 768c may be spaced from the porous main body 762. The hook 802b of the insulating member 802 may be disposed or provided between the fixing portion 768c and the porous main body 762. A bottom surface of the fixing portion 768c may contact a top surface of the hook 802b. As the fixing portion 768c may be latched to the insulating member 802, it is possible to prevent the holder 768 from being released from the insulating body 802a.

The lamp coupling portion 768b may be coupled to the UV lamp 764. The lamp coupling portion 768b may surround at least a portion of the external electrode 764a of the UV lamp 764. An inner surface of the lamp coupling portion 768b may surround at least a portion of an outer surface of the external electrode 764a of the UV lamp 764.

A method of coupling the lamp coupling portion 768b and the UV lamp 764 is not limited thereto. For example, a groove may be formed in the lamp coupling portion 768b, and the UV lamp 764 may be fitted into the groove.

The water-proof sealing 804 may include a first water-proof sealing or seal 804a that surrounds the fixing portion 768c of the holder 768, and a second water-proof sealing or seal 804b that surrounds a portion of the main body 768a, the lamp coupling portion 768b, and the external electrode 764a of the UV lamp 764. The first water-proof sealing 804a may further cover the hook 802b of the insulating member 802 that contacts the fixing portion 768c.

The second water-proof sealing 804b may surround a portion of the main body 768a of the holder 768 which is not disposed inside of the hollow 8020 of the insulating body 802a, the lamp coupling portion 768b, and the external electrode 764a of the UV lamp 764. The second water-proof sealing 804b may further surround the hook 805b fixed to the front surface of the porous main body 762.

In the UV sterilization module 760 according to this embodiment, the porous main body 762 may be more tightly coupled to the holder 768. Further, the UV lamp 764 and the porous main body 762 may be arranged to be closer to each other, and a more compact UV sterilization module 760 may be provided.

Figure 18:
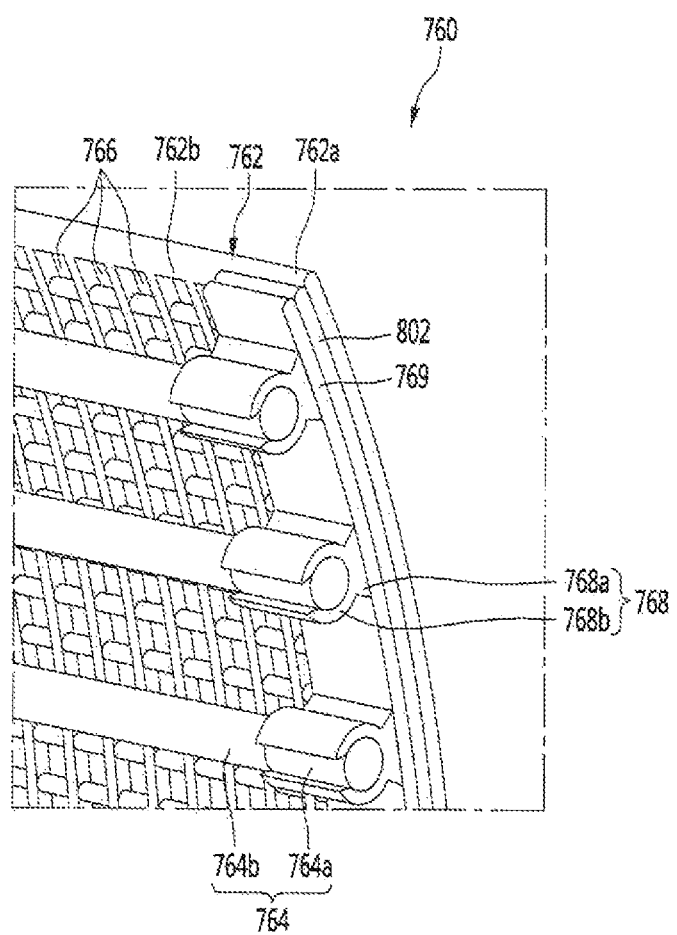
FIG. 18 is a diagram for describing a UV sterilization module according to yet another embodiment.
Figure 19:
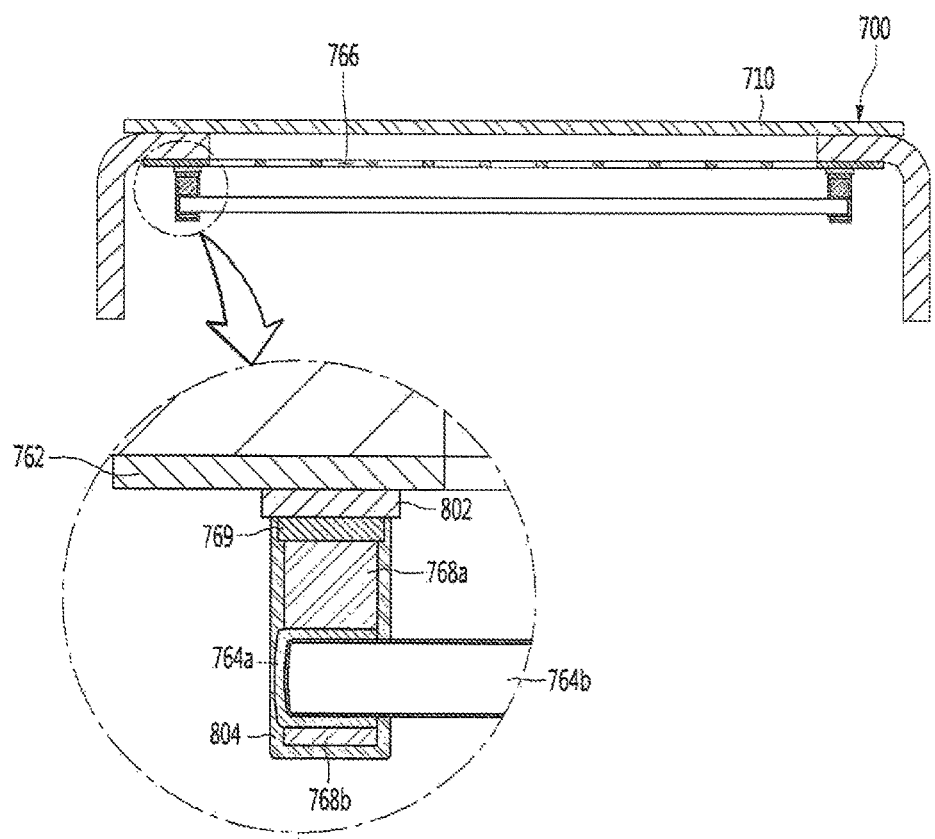
FIG. 19 is a vertical cross-sectional view for describing a UV sterilization module according to yet another embodiment.
Figure 20:
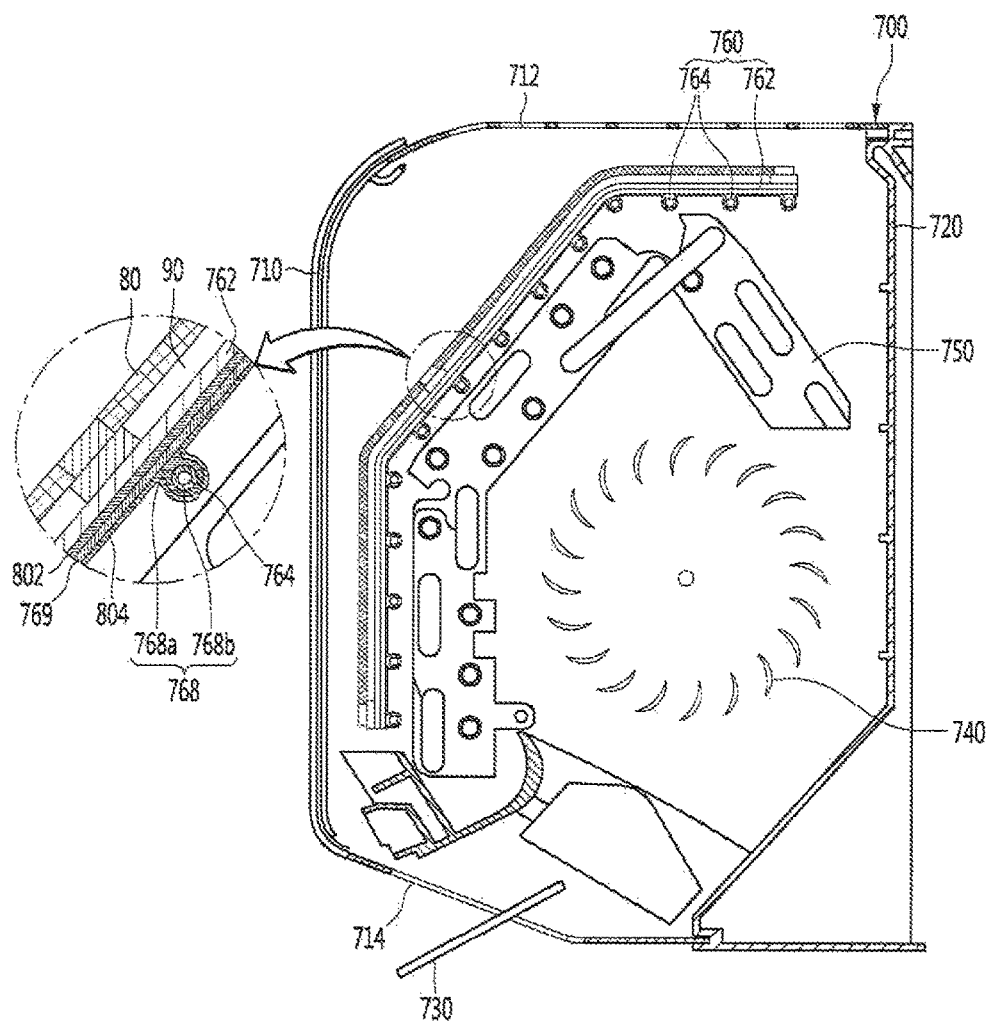
FIG. 20 is a horizontal cross-sectional view of an air conditioner including the UV sterilization module of FIG. 19.

FIG. 18 is a diagram for describing a UV sterilization module according to yet another embodiment. FIG. 19 is a vertical cross-sectional view for describing a UV sterilization module according to yet another embodiment. FIG. 20 is a horizontal cross-sectional view of an air conditioner including the UV sterilization module of FIG. 19.

The UV sterilization modules 760 according to the embodiments of FIGS. 18 and 19 are identical to each other, except for a configuration of sealing or seal 804. Thus, configurations and operations except for the sealing 804 will be simultaneously described. Further, descriptions of the same configurations and operations as those described above have been omitted, and the following descriptions will focus on differences.

Referring to FIGS. 18 to 20, each of the UV sterilization module 760 according to the embodiments of FIGS. 18 and 19 may include porous main body 762, UV lamp 764, a plurality of the holes 766 formed in air hole portion 762b, insulating member 802, and a conductive module 767. The conductive module 767 may be installed or provided in the insulating member 802 and may support the UV lamp 764.

When the holder 768 is a conductive holder, the conductive module 767 may include the holder 768. Alternatively, the conductive module 767 may include a metal rail 769 and holder 768 connected to the metal rail 769.

The metal rail 769 may be connected to a power supply and electricity may be conducted. Thus, the metal rail 769 may be referred to as a bus bar.

The metal rail 769 may be installed or provided in the porous main body 762. More specifically, the metal rail 769 may be installed or provided in the mounting portion 762a of the porous main body 762. The insulating member 802 may be provided in the mounting portion 762a of the porous main body 762, and the metal rail 769 may be installed or provided in the insulating member 802.

One pair of metal rails 769 may be arranged on one surface of the porous main body 762 so as to be spaced from each other. The metal rail 769 may extend in a direction perpendicular to a lengthwise direction of the UV lamp 764. That is, the metal rail 769 may be arranged to be elongated in a direction perpendicular to a length direction of the UV lamp 764.

The metal rail 769 may be a conductive material to which a current may be applied. At least one holder 768 may be connected to each of one pair of metal rails 769.

A plurality of metal rails 769 arranged in parallel may be provided in the porous main body 762. One of the plurality of UV lamps 764 may be electrically connected to any two of the plurality of metal rails 769.

A plurality of pairs of holders 768 may be connected to and installed in one pair of metal rails 769. More specifically, any one holder 768 of two holders 768 constituting any one pair may be installed in one metal rail 769 of one pair of metal rails 769, and the other holder 768 may be installed in the other metal rail 769.

The plurality of holders 768 may be installed in the metal rail 769 so as to be spaced from each other. That is, the plurality of holders 768 may be arranged in each of one pair of metal rails 769 at regular intervals.

When the material of the metal rail 768 is a conductive material, electricity may be conducted in the metal rail 769. In this case, the metal rail 769 may be electrically connected to the holder 768 and the external electrode 764a of the UV lamp 764. At this time, the holder 768 may be a conductive holder.

The electrical line may connect the metal rail 769 to the power supply, such as an inverter, so that electricity may be conducted in the metal rail 769. The electricity conducted in the metal rail 769 may be supplied to the external electrode 764a of the UV lamp 764 along the holder 768, and thus, the UV lamp 764 may be operated.

More specifically, one pair of metal rails 769 may be connected to the power supply, such as the inverter, through the electrical line, and thus, a potential difference may occur between one pair of metal rails 769. That is, the power supply may apply a voltage between one pair of metal rails 769. One pair of metal rails 769 may be electrically connected to the holders 768 respectively connected thereto, and the holders 768 may be electrically connected to the external electrodes 764a of the UV lamp 764. Therefore, a potential difference may occur between the external electrodes 764 of both ends of the UV lamp 764. As the UV lamp 764 has already been described above in detail, redundant descriptions thereof have been omitted.

The metal rails 769 may be a parallel connector for the plurality of UV lamps 764. More specifically, the plurality of UV lamps 764 may be arranged in parallel, and one pair of metal rails 769 may be arranged on both ends of the plurality of UV lamps 764 arranged in parallel. Further, the bus bars 769 may be electrically connected to the external electrodes 764a of the UV lamp 764.

Therefore, when electricity is conducted in one pair of metal rails 769, all the UV lamps 764 electrically connected in parallel to the metal rails 769 may be operated. That is, even though the electrical lines are not connected to the holders 768 or the external electrodes 764a of the UV lamp 764 one by one, the plurality of UV lamps 764 may be operated.

In the UV sterilization module 760, the insulating member 802 may be provided between the metal rail 769 and one surface of the porous main body 762 where the UV lamp 764 is arranged. That is, the metal rail 769 may be installed in the insulating member 802 provided in the mounting portion 762a of the porous main body 762. The insulating member 802 may prevent the current applied to the metal rail 769 from flowing through the porous main body 762.

When the insulating member 802 is not present, the current applied to the metal rail 769 may flow through the porous main body 762, thus causing short circuit or discharge. The insulating member 802 may be disposed or provided between the porous main body 762 and the conductive module 767. The insulating member 802 may be formed to be elongated in the lengthwise direction of the metal rail 769.

A plurality of the insulating member 802 may be provided, and the plurality of insulating members 802 may be spaced from each other. One or a first surface of the insulating member 802 may contact the metal rail 769, and the other or a second surface thereof may contact the porous main body 762.

An area of the insulating member 802 may be larger than an area of the metal rail 769. That is, only a portion of the one surface of the insulating member 802 may contact the metal rail 769.

Referring to FIGS. 19 and 20, the UV sterilization module 760 according to this embodiment may further include water-proof sealing or seal 804. The water-proof sealing 804 may surround the conductive module 767 and the external electrode 764a of the UV lamp 764 together. The water-proof sealing 804 may surround the metal rail 769, the holder 768, and the external electrode 764a of the UV lamp 764. The water-proof sealing 804 may surround the metal rail 769, the holder 768, and the external electrode 764a together. The water-proof sealing 804 may further surround the insulating member 802.

The water-proof sealing 804 may prevent corrosion caused when the metal rail 769, the holder 768, and the external electrode 764a of the UV lamp 764 are exposed to external moisture or foreign substances. Further, the water-proof sealing 804 may prevent the occurrence of short circuit or discharge in the metal rail 769, the holder 768, and the external electrode 764a of the UV lamp 764.

Figure 21:
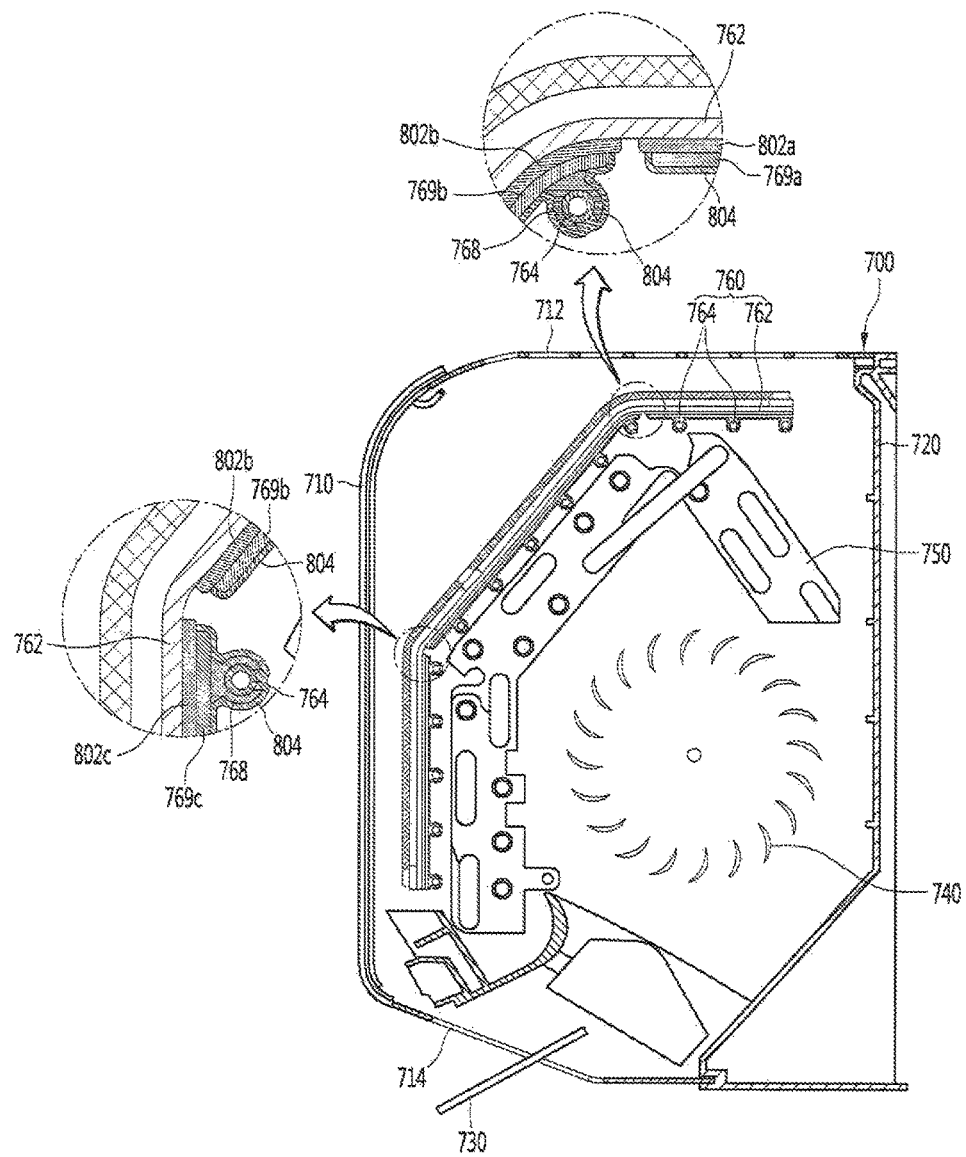
FIG. 21 is a horizontal cross-sectional view of an air conditioner including a UV sterilization module according to yet another embodiment.

FIG. 21 is a horizontal cross-sectional view of an air conditioner including a UV sterilization module according to yet another embodiment. The UV sterilization module 760 according to this embodiment may be identical to a configuration in which the metal rails 769 of the UV sterilization module 760 are separated into at least two metal rails 769 and are arranged to be spaced from each other. Hereinafter, redundant descriptions have been omitted.

The UV sterilization module 760 according to this embodiment may include a plurality of metal rails 769a, 769b, and 769c, respectively, electrically connected to UV lamps 764. More specifically, the plurality of metal rails 769a, 769b, and 769c may be arranged in the porous main body 762 so as to be spaced from each other with respect to a direction perpendicular to the lengthwise direction of the UV lamp 764. In this case, at least one holder 768 may be connected to each of the plurality of metal rails 769a, 769b, and 769c.

For example, the first metal rail 769a, the second metal rail 769b, and the third metal rail 769c may be arranged in the porous main body 762 so as to be spaced from each other. In this case, three, six, and five holders 768 and UV lamps 764 connected thereto may be, respectively, electrically connected to the first metal rail 769a, the second metal rail 769b, and the third metal rail 769c.

The insulating member 802 may be formed to be separated into at least two insulating members so as to correspond to the respective bus bars 768a, 768b, and 768c. That is, the UV sterilization module 760 may include a plurality of insulating members 802a, 802b, and 802c arranged between the plurality of metal rails 769a, 769b, and 769c and the porous metal body 762.

For example, the insulating member 802 may be formed to be separated into the first insulating member 802a, the second insulating member 802b, and the third insulating member 802c. Alternatively, the insulating member 802 may be integrally formed without being separated. The water-proof sealing 804 may surround the metal rails 769a, 769b, and 769c, the holders 768 installed in the metal rails 769a, 769b, and 769c, and the external electrodes 764a of the UV lamps 764 connected to the holders 768.

It is obvious that the number of UV lamps 764 connected to the metal rails 769a, 769b, and 769c may be changed. The number of metal rails 769 may also be changed.

In the metal rails 769a, 769b, and 769c, electricity may be conducted by a power supply, such as an inverter. When the current is applied to the metal rails 769a, 769b, and 769c through the electrical line connected to the power supply, the current flows through the holders 768 and the external electrodes 764a of the UV lamps 764 connected to the metal rails 769a, 769b, and 769c. Thus, the UV lamps 764 connected to the metal rails 769a, 769b, and 769c are operated.

For example, when the current is applied to the first metal rail 769a, the three UV lamps 764 connected to the first metal rail 769a are operated. When the current is applied to the second metal rail 769b, the six UV lamps 764 connected to the second metal rail 769b are operated. When the current is applied to the third metal rail 769c, the five UV lamps 764 connected to the third metal rail 769c are operated.

The three UV lamps corresponding to the first metal rail 769a may be arranged to face an upper rear portion of the heat exchanger 750. The six UV lamps corresponding to the second metal rail 769b may be arranged to face an upper front portion of the heat exchanger 750. The five UV lamps corresponding to the third metal rail 769c may be arranged to face a vertical portion of the heat exchanger 750.

Therefore, it is possible to respectively operate a specific number of the UV lamps among the total UV lamps 764 or the UV lamps 764 of a specific region. Further, a region to be sterilized in the heat exchanger 750 may be specified, and the UV lamps 762 corresponding to the specified region may be operated. That is, sterilization intensity or sterilization positions in the air conditioner may be separately set according to the number of UV lamps 764 to be operated.

Figure 22:
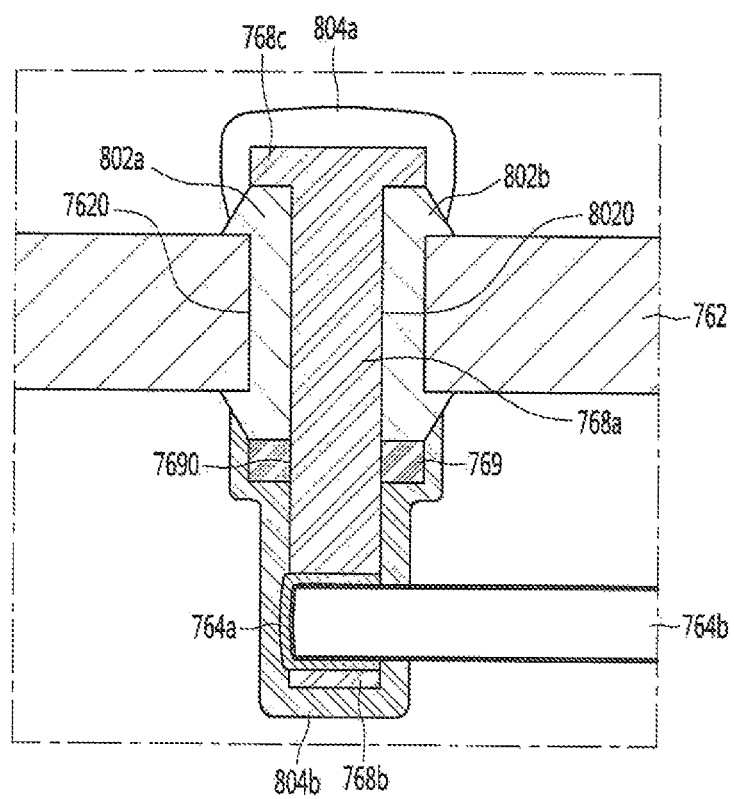
FIG. 22 is a vertical cross-sectional view for describing a UV sterilization module according to yet another embodiment.
Figure 23:
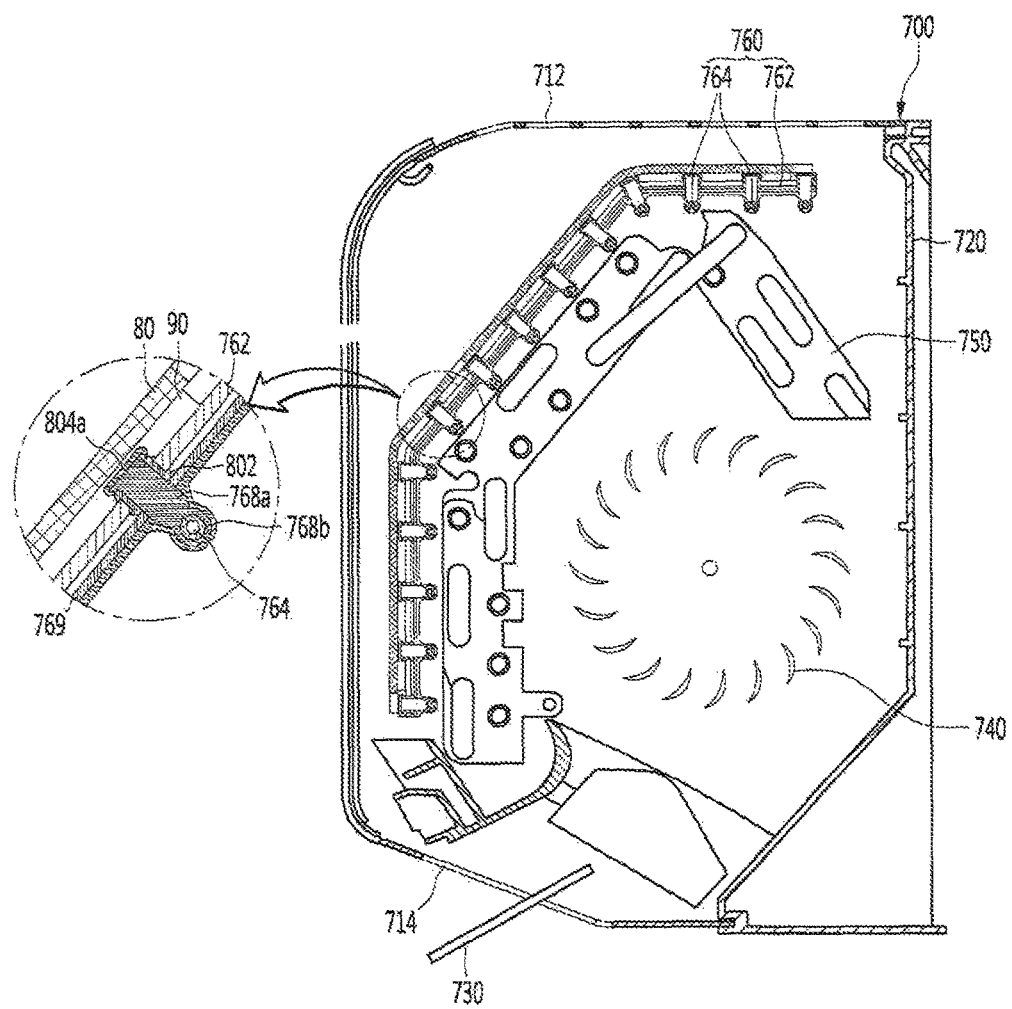
FIG. 23 is a horizontal cross-sectional view of an air conditioner including the UV sterilization module of FIG. 22.

FIG. 22 is a vertical cross-sectional view for describing a UV sterilization module according to yet another embodiment. FIG. 23 is a horizontal cross-sectional view of an air conditioner including the UV sterilization module of FIG. 22.

The UV sterilization module 760 according to this embodiment may be identical to the UV sterilization module 760 of FIG. 16, except for configurations related to UV sterilization module 760 and metal rail 769. Thus, redundant descriptions have been omitted and the following descriptions will focus on differences.

Referring to FIGS. 22 and 23, insulating member 802 may include insulating body 802a having hollow 8020 into which at least a portion of the conductive module 767 may be inserted, and hook 802b formed in the insulating body 802a and fixed to porous main body 762. The hook 802b may be formed on both ends of the insulating body 802a. In this case, the conductive module 767 may include holder 768 and metal rail 769.

The metal rail 769 may have holder connection hole 7690 to which a main body 768a of the holder 768 may be connected. More specifically, a portion of the main body 768a of the holder 768 may be inserted into the holder connection hole 7690. A side surface of the main body 768a of the holder 768 inserted into the holder connection hole 7690 may contact an inner surface of the holder connection hole 7690. Therefore, the metal rail 769 may be electrically connected to the holder 768. A portion of the main body 768a may be inserted into the hollow 8020, and another portion of the main body 768a may be inserted into the holder connection hole 7690.

The holder connection hole 7690 may have a same shape as the hollow 8020 formed in the insulating body 802a. An upper edge of the holder connection hole 7690 may contact a lower edge of the hollow 8020 formed in the insulating body 802a.

One surface of the metal rail 769 may contact the hook 802b of the insulating member 802. The fixing portion 768c of the holder 768 may contact the hook formed at one or a first end of the insulating body 802a, and the metal rail 769 may contact the hook 802b formed at the other or a second end of the insulating body 802a.

The metal rail 769 may contact the hook 802b of the insulating member 802 and may be spaced from the porous main body 762. Therefore, electricity conducted in the metal rail 769 may not flow through the porous metal body 762.

The UV sterilization module 760 may include first waterproof sealing or seal 804a and second water-proof sealing or seal 804b. The first water-proof sealing 804a may surround the fixing portion 768c of the holder 768. The second water-proof sealing 804b may surround the metal rail 769, a portion of the main body 768a of the holder 768 which is not inserted into the hollow 8020 of the holder connection portion 7690, the lamp coupling portion 768b, and the external electrode 764a of the UV lamp 764.

A plurality of holders 768 may be connected to the metal rail 769, and the UV sterilization module 760 may include the first water-proof sealing 804a, which surrounds the fixing portion 768c of each of the plurality of holders 769. That is, a plurality of the first water-proof sealing 804a may be provided, and the plurality of first water-proof sealings 804a may be spaced from each other.

The UV sterilization module 760 may include a single first sealing or seal 804a that surrounds the plurality of holders 768 and the fixing portions 768c together. The second water-proof sealing 804b may be a single sealing that surrounds the metal rail 769, the main bodies 768a and the lamp coupling portions 768b of the plurality of holders 768, and the external electrodes of the plurality of UV lamps 764 together.

In the air conditioners, configurations and methods of the embodiments described above are not limitedly applied, but all or part of the embodiments may be selectively combined so as to achieve various modifications.

Embodiments disclosed herein prevent a current from flowing toward a porous main body, the current being applied to a conductive module that supports an UV lamp. Embodiments disclosed herein also prevent corrosion of a conductive module and an external electrode of a UV lamp, and occurrence of short circuit or discharge. Embodiments disclosed herein operate a plurality of UV lamps without connecting individual electrical lines to a plurality of UV lamps.

A UV sterilization module according to embodiments disclosed herein may include a porous main body; a plurality of UV lamps having external electrodes; a plurality of conductive holders connected to the external electrodes and supporting the plurality of UV lamps to be spaced from the porous main body; and a bus bar connected to the plurality of conductive holders and disposed or provided between the conductive holders and the porous main body. The plurality of UV lamps may be arranged in parallel side by side. The plurality of conductive holders may be spaced from each other. The conductive holders may at least partially surround the external electrodes.

The bus bar may be elongatedly arranged in a direction perpendicular to a length direction of the UV lamp. A plurality of bus bars may be arranged on the porous main body so as to be spaced from each other with respect to a direction perpendicular to the length direction of the UV lamp, and at least one conductive holder may be connected to each of the plurality of bus bars. The porous main body may be a conductor and may further include an insulating member arranged between the porous main body and the bus bar.

A UV sterilization module according to embodiments disclosed herein may include a main body; a UV lamp supported to be spaced from the main body; a conductive module which supports the UV lamp; and an insulating member disposed or provided between the main body and the conductive module. The main body may include an air hole portion having a plurality of holes which allow air to pass through and on which UV rays emitted by the UV lamp may be radiated; and a mounting portion or mount which provides a path through which power supplied to the UV lamp may pass. The conductive module may include a bus bar installed in the insulating member, and a conductive holder including a lamp coupling portion that supports the UV lamp and a main body portion or main body connected to the bus bar.

The UV sterilization module may further include a water-proof sealing that surrounds both the conductive module and the external electrode. The insulating member may include an insulating body having a hollow into which at least a portion of the conductive module may be inserted and a hook formed in the insulating body and fixed to the porous main body.

The conductive module may include a conductive holder that supports the UV lamp, and the conductive holder may include a main body, at least a portion of which may be disposed or provided in the hollow, a lamp coupling portion formed at one or a first side of the main body and fixing the UV lamp; and a fixing portion formed at the other or second side of the main body and latched to the insulating member. The conductive module may further include a bus bar having a holder connection hole. At least a portion of the main body may be inserted into the holder connection hole. The bus bar may be disposed or provided between the insulating member and the lamp coupling portion.

A UV sterilization module according to embodiments disclosed herein may include a porous main body; a UV lamp disposed or provided to be spaced from the porous main body; a holder that supports the UV lamp and disposed or provided in the porous main body; and a water-proof sealing or seal that surround the holder and the external electrode. The water-proof sealing may be made of a thermosetting resin.

An air conditioner according to embodiments disclosed herein may include a main body having an air inlet and an air outlet; and a UV sterilization module provided in the main body. The UV sterilization module may include a main body; a UV lamp disposed or provided to be spaced from the main body; an insulating member provided in the main body; and a conductive module disposed or provided in the insulating member and that supports the UV lamp. The air conditioner may further include a heat exchanger provided in the main body and disposed or provided between the UV sterilization module and the air outlet.

The UV lamp may be disposed or provided between the main body and the heat exchanger. The main body may have at least one curve so as to correspond to a shape of the heat exchanger. The UV lamp may be plural, and the conductive module may include a plurality of conductive holders that supports the plurality of UV lamps; and a bus bar connected to the plurality of conductive holders.

According to embodiments disclosed herein, as the insulating member may be disposed or provided between the conductive module and the porous main body, a current applied to the conductive holder does not flow through the porous main body. Further, as the water-proof sealing may be provided to surround both the conductive module and the external electrode of the UV lamp, it is possible to prevent corrosion of the conductive holder and the external electrode of the UV lamp, or occurrence of short circuit or discharge. Furthermore, as the bus bar may be a parallel connector for the plurality of UV lamps, the plurality of UV lamps may be operated at a same time when current is applied to the bus bar.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultraviolet (UV) sterilization module, comprising:
   a porous main body;
   a plurality of UV lamps having external electrodes;
   a plurality of conductive holders connected to the external electrodes and that supports the plurality of UV lamps to be spaced from the porous main body; and
   at least one bus bar connected to the plurality of conductive holders and provided between the plurality of conductive holders and the porous main body.

2. The UV sterilization module of claim 1, wherein the plurality of UV lamps is arranged in parallel side by side.

3. The UV sterilization module of claim 1, wherein the plurality of conductive holders is spaced from each other.

4. The UV sterilization module of claim 1, wherein the plurality of conductive holders at least partially surrounds the external electrodes.

5. The UV sterilization module of claim 1, wherein the at least one bus bar is elongated in a direction perpendicular to a direction in which the plurality of UV lamps extends lengthwise.

6. The UV sterilization module of claim 1, wherein the at least one bus bar includes a plurality of bus bars arranged on the porous main body so as to be spaced from each other with respect to the direction perpendicular to the direction in which the plurality of UV lamps extends lengthwise, and wherein at least one conductive holder of the plurality of conductive holders is connected to each of the plurality of bus bars.

7. The UV sterilization module of claim 1, wherein the porous main body is a conductor and further includes an insulating member arranged between the porous main body and the at least one bus bar.

8. An air conditioner including the UV sterilization module of claim 1.

9. An ultraviolet (UV) sterilization module, comprising:
   a main body;
   at least one UV lamp supported to be spaced from the main body;
   a conductive module that supports the at least one UV lamp;
   an insulating member provided between the main body and the conductive module; and a water-proof seal that surrounds both the conductive module and an external electrode of the at least one UV lamp, wherein the main body includes:
  an air hole portion having a plurality of holes that allows air to pass therethrough and onto which UV rays emitted by the at least one UV lamp are radiated; and
  a mounting portion that provides a path through which power is supplied to the at least one UV lamp.

10. The UV sterilization module of claim 9, wherein the conductive module includes:
  a bus bar provided on the insulating member; and
  at least one conductive holder including a lamp coupling portion that supports the at least one UV lamp and a main body connected to the bus bar.

11. The UV sterilization module for claim 9, wherein the insulating member includes:
  an insulating body having a hollow into which at least a portion of the conductive module is inserted; and
  a hook formed in the insulating body and fixed to the main body.

12. The UV sterilization module of claim 11, wherein the conductive module includes at least one conductive holder that supports the at least one UV lamp, and the at least one conductive holder includes:
  a main body having at least a portion of which is provided in the hollow;
  a lamp coupling portion formed at a first side of the main body portion and that fixes the at least one UV lamp; and
  a fixing portion formed at a second side of the main body and latched to the insulating member.

13. The UV sterilization module of claim 12, further including a bus bar having a holder connection hole, wherein at least a portion of the main body is inserted into the holder connection hole, and the bus bar is provided between the insulating member and the lamp coupling portion.

14. An air conditioner including the UV sterilization module of claim 9.

15. An ultraviolet (UV) sterilization module, comprising:
  a porous main body;
  at least one UV lamp spaced from the porous main body;
  at least one holder that supports the at least one UV lamp and provided on the porous main body; and
  a water-proof seal that surrounds the at least one holder and an external electrode of the at least one UV lamp.

16. The UV sterilization module of claim 15, wherein the water-proof seal is made of a thermosetting resin.

17. An air conditioner including the UV sterilization module of claim 15.

18. An air conditioner, comprising:
  a main body having an air inlet and an air outlet; and
  a UV sterilization module provided in the main body, wherein the UV sterilization module includes:
  a main body;
  at least one UV lamp provided spaced from the main body;
  an insulating member provided on the main body; and
  at least one conductive module provided on the insulating member and that supports the at least one UV lamp, wherein the at least one UV lamp includes a plurality of UV lamps, and the at least one conductive module includes:
    a plurality of conductive holders that supports the plurality of UV lamps; and
    at least one bus bar connected to the plurality of conductive holders.

19. The air conditioner of claim 18, further including a heat exchanger provided in the main body and provided between the UV sterilization module and the air outlet.

20. The air conditioner of claim 19, wherein the at least one UV lamp is provided between the main body and the heat exchanger.

21. The air conditioner of claim 19, wherein the main body has at least one curve so as to correspond to a shape of the heat exchanger.

22. The air conditioner of claim 18, wherein the air conditioner is one of a stand-type air conditioner, a wall-mounted air conditioner, or a ceiling-mounted air conditioner.

23. An ultraviolet (UV) sterilizer, comprising:
  a porous main body;
  a plurality of UV lamps arranged side by side and each having first and second external electrodes;
  a plurality of conductive holders connected to the first and second external electrodes and that supports the plurality of UV lamps to be spaced from the porous main body;
  at least one bus bar connected to the plurality of conductive holders and provided between the plurality of conductive holders and the porous main body; and
  an insulating member arranged between the porous main body and the at least one bus bar.

24. An air conditioner including the UV sterilizer of claim 23.

* * * * *